(12) United States Patent
Gobaille et al.

(10) Patent No.: US 7,122,326 B2
(45) Date of Patent: Oct. 17, 2006

(54) IDENTIFICATION OF MODULATORS OF NEUROTRANSMITTER ACTIVITY OF XANTHURENIC ACID

(75) Inventors: Serge Gobaille, Vendenheim (FR); Michel Maitre, Strasbourg (FR)

(73) Assignee: Universite Louis Pasteur, Strasbourg (FR)

( * ) Notice: Subject to any disclaimer, the term of this patent is extended or adjusted under 35 U.S.C. 154(b) by 0 days.

(21) Appl. No.: 10/481,595

(22) PCT Filed: Jul. 4, 2002

(86) PCT No.: PCT/FR02/02337

§ 371 (c)(1),
(2), (4) Date: Dec. 23, 2003

(87) PCT Pub. No.: WO03/005038

PCT Pub. Date: Jan. 16, 2003

(65) Prior Publication Data

US 2004/0157917 A1    Aug. 12, 2004

(30) Foreign Application Priority Data

Jul. 5, 2001    (FR) .................................. 01 08937

(51) Int. Cl.
*G01N 33/567*    (2006.01)
(52) U.S. Cl. ...................................... 435/7.2
(58) Field of Classification Search ................ 435/7.2, 435/7.93, 7.95, 16, 121
See application file for complete search history.

(56) References Cited

FOREIGN PATENT DOCUMENTS

| WO | WO 95/03271 | 2/1995 |
|---|---|---|
| WO | WO 98/02553 | 1/1998 |
| WO | WO 98/51290 | 11/1998 |
| WO | WO 00/73788 | 12/2000 |

OTHER PUBLICATIONS

Malina, H., Bichem. Biophys. Res. Comm. 265 : 600-605, 1999.*
Dermer, G., Bio/Technology, 12: 320, 1994.*
Jain, R., Cancer and Metastasis Reviews, 9: 253-266, 1990.*
Miller et al, Role of High-Affinity Dopamine Uptake and Impulse Activity in the Appearance of Extracellular Dopamine in Striatum After Administration of Exogenous L-DOPA: Studies in Intact and 6 Hydroxydopamine-Treated Rats, Journal of Neurochemistry, vol. 72, No. 4, Apr. 1999, pp. 1516-1522.

* cited by examiner

*Primary Examiner*—Eileen B. O'Hara
*Assistant Examiner*—Gyan Chandra
(74) *Attorney, Agent, or Firm*—Nixon & Vanderhye P.C.

(57) ABSTRACT

The invention relates to methods and compositions for the selection and development of novel pharmacological agents or novel medicaments having properties or mechanisms of action which are original. The invention specifically describes the characterization and identification of the functional role of several constitutive elements of the central nervous system playing a role in the metabolism or transport of xanthurenic acid (XA) or involved in receiving and/or transducing the signal mediated by this substance. Said targets are new tools for the definition and selection of novel synthetic chemical substances, interfering with said targets and modulating the functions of XA in order to benefit from the pharmacological or medicamentous advantages thereof. The invention can be primarily used to treat neurological or mental pathologies or diseases.

5 Claims, 25 Drawing Sheets

Figure 1:
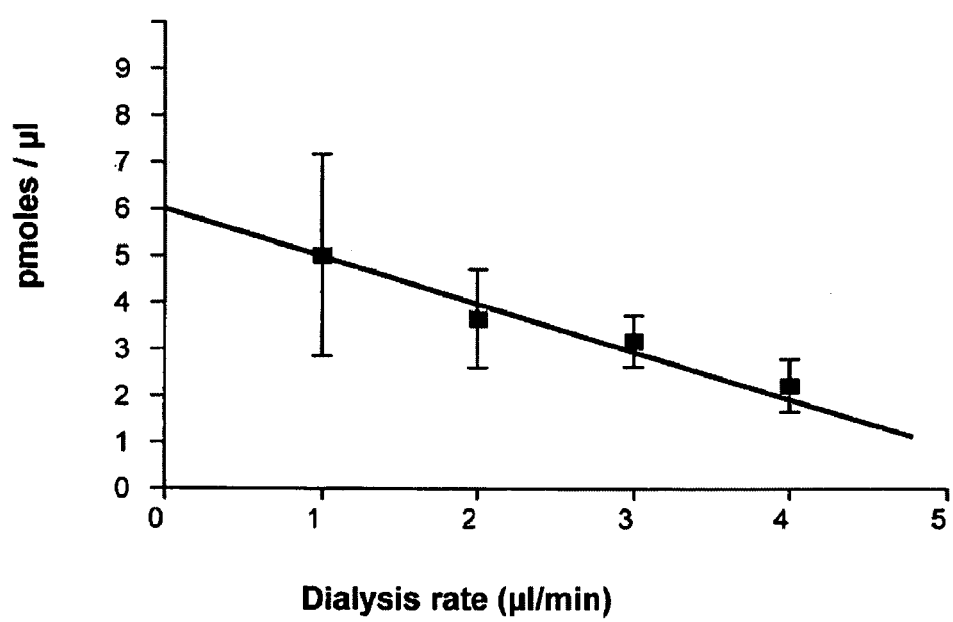

- 0.1 – 0.5 nmoles /g
- 0.5 – 1.0 nmoles /g
- 0.5 – 1.0 nmoles /g
- \> 1 nmoles /g

|  | TB | NSB | SB |
|---|---|---|---|
| YMAX | 9564 | 5865 | 3482 |
| K | 0.6168 | 0.8860 | 0.5397 |
| HalfLife | 1.124 | 0.7824 | 1.284 |
| Std. Error |  |  |  |
| YMAX | 232.6 | 145.6 | 210.4 |
| K | 0.08527 | 0.1801 | 0.1675 |
| Goodness of Fit |  |  |  |
| Degrees of Freedom | 24 | 25 | 19 |
| $R^2$ | 0.9225 | 0.9049 | 0.7541 |

|  | T | NS | S |
|---|---|---|---|
| BMAX | 32.01 | 76.67 | 6.960 |
| KD | 1.9210e-006 | 8.8370e-006 | 7.4310e-007 |
| Std. Error |  |  |  |
| BMAX | 7.059 | 76.23 | 1.237 |
| KD | 5.9230e-007 | 9.6130e-006 | 2.4980e-007 |
| Goodness of Fit |  |  |  |
| Degrees of Freedom | 19 | 19 | 12 |
| $R^2$ | 0.9810 | 0.9779 | 0.9642 |

|  | T | NS | S |
|---|---|---|---|
| BMAX | 867.9 | 410.6 | 581.8 |
| KD | 9.1610e-006 | 2.3220e-005 | 7.5600e-006 |
| Std. Error |  |  |  |
| BMAX | 50.18 | 609.6 | 33.57 |
| KD | 9.3210e-007 | 3.5760e-005 | 8.2100e-007 |
| Goodness of Fit |  |  |  |
| Degrees of Freedom | 25 | 16 | 25 |
| $R^2$ | 0.9942 | 0.9929 | 0.9922 |

Open field test

IDENTIFICATION OF MODULATORS OF NEUROTRANSMITTER ACTIVITY OF XANTHURENIC ACID

This application is the US national phase of international application PCT/FR02/02337 filed 4 Jul. 2002 which designated the US and claims benefit of FR 0108937, dated 5 Jul. 2001, the entire contents of each of which is hereby incorporated by reference.

The invention relates to methods and compositions for the selection and development of novel pharmacological agents or novel medicaments having properties or mechanisms of action which are original. The invention specifically describes the characterization and identification of the functional role of several constitutive elements of the central nervous system playing a role in the metabolism or transport of xanthurenic acid (XA) or involved in receiving and/or transducing the signal mediated by this substance. Said targets are new tools for the definition and selection of novel synthetic chemical substances, interfering with said targets and modulating the functions of XA in order to benefit from the pharmacological or medicamentous advantages thereof. The invention can be primarily used to treat neurological or mental pathologies or diseases.

The pharmaceutical industry is continually in search of new natural substances, present in the brain, and which have an important functional role in the regulation and control of psychological, psychoaffective, mental, cognitive or neurological activity. The discovery of new mechanisms of neurotransmission and novel targets participating in said mechanisms within the nervous system are just so many valuable tools for the selection of novel medicaments in diverse indications to be described hereinbelow. The present invention describes for the first time the important role of a natural substance, xanthurenic acid, in central neurotransmission phenomena. This new neurotransmission system comprises a metabolic system for synthesis and elimination of the transmitter, transporters, receptors and intracellular signals switched on upon stimulation of said receptors. Such components constitute "targets" which may be modulated by potential medicaments and used for the identification, selection or characterization of biologically active compounds. Moreover, the invention also describes different functional roles of xanthurenic acid in the brain (interference with other neurotransmitters, role in some behavioral or neuropharmacological protocols) allowing to envision novel pharmacological or therapeutic uses for said molecule, its derivatives or, more generally, natural or synthetic substances which bind to the hereinabove targets.

Since the early 1980s, tryptophan catabolism has gradually assumed an ever more prominent role in research on the causes and treatments of major central nervous system disorders (Orv. Hetil. 1992, July 19; 133 (29): 1803–1807). It is mainly compounds such as quinolinic acid and kynurenic acid, which are tryptophan metabolites, that have been the focus of attention by virtue of their pharmacological profiles. An imbalance in the formation of these metabolites, a chronically altered synthesis or degradation, may underlie functional disturbances of the central nervous system and the resultant pathologies.

In the case of XA, another tryptophan metabolite, different studies have reported various effects of XA. For instance, XA (50–600 mg/kg i.p.) was described as having an analgesic effect in Sprague-Dawley rats in the hotplate ("plaque chaude") and tail flick tests (Pharmacol. Res. 1998, October; 38 (4): 243–250). Moreover, in animals, intraperitoneal injection of XA prolonged the latency time to onset of epileptic seizures induced by intracerebroventricular injection of quinolinic acid, strychnine or pentylenetetrazole. It would seem that increased excretion of XA fulfils a compensation process in patients manifesting different stages of convulsive episodes (J. Neurol. Transm. 1983; 56 (2–3): 177–185; Clin. Endocrinol. (Oxf) 1997, December; 47 (6): 667–677). After an oral dose of tryptophan (5 g), 24-hour urinary excretion of XA was markedly increased in depressed patients (Psychopharmacology (Berl) 1981; 75 (4): 346–349; Acta Psychiatr. Belg. 1979, November–December; 79 (6): 638–646). Other results show however that ICV injection of XA does not modify the ECG in rats (Okayama Igakkai Zasshi 104 (5–6): 471–482, 1992), that injection of XA in mice does not induce head twitch behavior (Psychopharmacology (Berl) 1977, March 16; 51 (3): 305–309), that XA does not block depolarizations induced by excitatory amino acids (Brain Res. 1986; August 20; 380 (2): 297–302) and that XA induces an increase in the expression of an endoplasmic reticulum chaperone protein (Grp 94) and of calreticulin, causing an abnormal conformation of some proteins. The xanthurenic acid concentrations required to produce these effects in cultured cells are in the millimolar range (H. Malina; Biochem. Biophys. Res. Comm., 1999, 265: 600–605).

However, to date, the role of XA has yet to be characterized, its mode of action and its physiological role are still obscure, the possible existence of a receptor has not been demonstrated, and no therapeutic strategy based on this molecule has been undertaken.

The present invention results from the description, characterization and identification of the functional role of several constitutive elements of the central nervous system, playing a role in the metabolism or transport of xanthurenic acid (XA) or involved in receiving and/or transducing the signal mediated by this substance. These targets are new tools for the definition and selection of novel synthetic chemical substances, interfering with said targets and modulating the functions of XA in order to benefit from the pharmacological and medicamentous advantages thereof. The invention more particularly demonstrates the role of XA in the central nervous system and its involvement, as a neurotransmitter, in many pathophysiological mechanisms. The invention demonstrates in particular:

- the existence and characteristics of extracellular release of XA in the cortex,
- the existence of a high affinity binding site for this substance in brain, modulated by adenylate derivatives (adenosine, ADP, ATP), copper and zinc ions, and kynurenic acid and its derivatives,
- the existence of functional interrelationships in vivo between XA and dopamine in the brain, allowing in particular to propose a role for XA nerve terminals in the frontal cortex in regulating the dopaminergic system, in particular via an impact on glutamatergic and GABAergic activities. XA induces dose-dependent dopaminergic stereotypies when administered in the $A_{10}$ nucleus, or in the nucleus accumbens, striatum and lateral ventricles. This points to the XA system as an important target for ligands of the corresponding receptor sites, said ligands regulating glutamate/GABA/dopamine activites involved in the production of schizophrenic symptoms. It might therefore be expected that XA receptor ligands will be of major interest for the treatment of certain psychotic symptoms, induction of electrophysiological effects by micromolar concentrations of XA on certain membrane ion conductances in cells expressing XA receptors, demonstration of sodium-dependent active transport of XA in cultured neurons. This function represents a novel target for structural analogs of XA, or more generally for synthetic ligands interfering with said transport system. In fact, inhibition of this transport system can result in an increased half-life of XA in certain functional compartments in brain, particularly the synaptic compartment. Inhibitors of this transport system may therefore represent a novel class of substances having beneficial effects in several types of neurological or mental pathologies,
- reactions to an acute stress lead not only to extracellular release of norepinephrine, but also to a marked release of XA. Release of the latter substance participates in producing adaptation reactions to said stress. The results therefore indicate that ligands modulating the activity of the XA system may be useful in man for regulating reactions to stress.
- the ability of synthetic XA agonists to induce XA-type electrophysiological effects in NCB-20 cells and, in particular, to modulate cerebral dopamine in vivo,
- the ability of XA antagonists, such as NCS-486, to antagonize the electrophysiological effects induced by XA or its agonists, and in particular to inhibit the dopaminergic activity of XA in vivo, and
- the specific neuropharmacological effects of XA in vivo, after local application or systemic administration, which induces sedation, anxiolysis, dopaminergic effects (which may be useful in several areas such as drug addiction, Parkinson's disease, schizophrenia, mood disorders, and the like), antidepressant effects and beneficial effects on memory and social interactions.

The present application thereby demonstrates that XA, for which no functional role had so far been identified in the CNS (central nervous system), has properties that strongly suggest a role as a neurotransmitter/neuromodulator. This new neurotransmission/neuromodulation system offers an array of potential targets (enzymes that synthesize and degrade XA, receptor sites, transport sites, sites of release) for ligands or compounds, of synthetic or natural origin, modulating the activity of XA and, for this reason, representing potential medicaments in the therapy of neurological and mental disorders.

The present application therefore has as its object the use of a compound modulating the activity of xanthurenic acid for preparing a medicament for treating nervous system pathologies. The invention also concerns a method for treating pathologies of the nervous system, particularly central, comprising administering to a subject a compound modulating the activity of xanthurenic acid.

A particular aspect of the invention is based on the use a compound specifically modulating xanthurenic acid activity for preparing a medicament for treating nervous system pathologies, and on a corresponding method of treatment. The compound is called specific when it modulates foremost the activity of XA [e.g., its transport, its metabolism or the activity of XA receptor(s)] without being primarily intended to have a significant, direct effect on the activity of other central neurotransmission/neuromodulation systems. Of course, modulation of the central XA system leads to consequences and adaptations in other systems, in particular the dopaminergic or GABAergic system, but not substantially in the serotoninergic system. Particular specific compounds according to the invention are compounds able to preferentially bind to an XA receptor without binding, in a specific or substantial manner, to a serotoninergic receptor or other receptor of other neurotransmitters/neuromodulators.

According to preferred modes of embodiment, the invention has more particularly as its object:

- the use of a compound modulating xanthurenic acid activity for preparing a medicament for treating anxiety, and a corresponding method of treatment;
- the use of a compound modulating xanthurenic acid activity for preparing a medicament for treating depression, and a corresponding method of treatment;
- the use of a compound modulating xanthurenic acid activity for preparing a medicament for treating impairment of memory or social interactions, and a corresponding method of treatment;
- the use of a compound modulating xanthurenic acid activity for preparing a sedative and/or hypnotic medicament, in particular a compound which potentiates the neuropharmacological effect of XA, preferably a compound which is an allosteric activator of the XA receptor, and a corresponding method of treatment;
- the use of a compound modulating xanthurenic acid activity for preparing a medicament for modulating dopaminergic action, and a corresponding method of treatment;
- the use of a compound modulating xanthurenic acid activity for preparing a medicament for treating psychotic symptoms, particularly schizophrenia, and a corresponding method of treatment;
- the use of a compound modulating xanthurenic acid activity for preparing a medicament for regulating reactions to stress, and a corresponding method of treatment;
- the use of a compound modulating xanthurenic acid activity for preparing a medicament for regulating behavioral arousal, and a corresponding method of treatment;

Within the context of the invention, the term "treatment" denotes preventive, curative, palliative treatment as well as management of patients (alleviating suffering, prolonging survival, improving quality of life, slowing disease progression), etc. Furthermore, the treatment may be carried out in combination with other agents or treatments, particularly addressing the late events of the disease, or with other active substances. As noted hereinabove, the compounds used are preferably specific modulators of XA activity.

The invention also has as its object a method for modulating the dopaminergic effects of XA comprising administering to a subject a compound modulating the activity of xanthurenic acid.

A further object of the invention is the use of a compound modulating xanthurenic acid activity for preparing a medicament for treating neurodegenerative diseases, particularly Parkinson's disease, Alzheimer's disease or ALS, mental illnesses, such as schizophrenia, or else some drug dependencies, particularly opioid.

The invention equally concerns a method for modulating XA activity in vivo, comprising administering to a subject an efficacious dose of a synthetic compound modulating XA activity.

In the context of this application, the term "modulation" denotes either a stimulation, or an inhibition of XA activity. Stimulation may be achieved by using compounds mimicking the activity of XA or stimulating the quantity or efficacy of XA. Inhibition may be partial (eg., a reduction of activity). It may be achieved by decreasing the amount of XA present or by inhibiting the ability of XA to produce a biological effect, or by blocking or inhibiting the biological effect induced by XA.

For this reason, in the context of the present application, the term "xanthurenic acid activity" denotes in particular the synthesis of this compound, its transport, its release, its interaction with a receptor or with a partner, its degradation, a signal or metabolic pathway activated or regulated by XA, and the like, that is to say, the activity of the system using XA as mediator. The compound modulating XA activity may therefore be an agent that modulates XA synthesis, an agent modulating XA transport or release, an XA agonist, an XA antagonist, and the like. It may also be a compound that modulates the activity of the XA receptor site by acting on a regulatory or allosteric site of said receptor.

According to a first specific embodiment, the compound used is a compound modulating the synthesis or regulation of XA. Such compound may act on the activity or expression of enzymes involved in the biosynthesis of this molecule or its precursors, in particular a compound modulating the activity of kynurenin-3-hydroxylase. This enzyme plays a role in regulating XA production, and its modulation by the compounds enables modulation of XA activity, within the context of the present application. Compounds modulating the activity or expression of this enzyme are for instance antisense molecules, transcriptional inhibitors, ribozymes or aptazymes, anti-protein antibodies, chemical or peptide compounds able to inhibit the activity of the enzyme, etc.

According to another particular embodiment, the compound used is a compound modulating the binding of XA to a membrane receptor (eg., an agonist or antagonist). An agonist is a compound displaying an affinity for the XA binding site, and producing a signal analogous to that produced by XA. An antagonist is a compound displaying an affinity for the XA binding site, and preventing binding and signal production by XA or an XA agonist. Such compounds may be XA analogs, anti-XA antibodies, synthetic compounds and the like. Thus, a compound modulating XA binding to a membrane receptor implicates the XA system as an important target for ligands of the corresponding receptor sites, said ligands regulating glutamate/GABA/dopamine activities involved in the production of schizophrenic symptoms. XA receptor ligands are of particular interest for treating certain psychotic symptoms. XA receptor antagonist compounds find use more specifically in regulating behavioral arousal and in certain mental illnesses or in hyper-dopaminergic states. Such compounds may be identified, synthesized, or characterized by the methods described hereinbelow.

Another usable compound according to the invention is a compound modulating XA transport or release. Such compounds, by reducing or facilitating XA release, allow local modulation of XA activity, in the context of the invention. Other synthetic molecules, having in some cases structural analogies with XA, may interfere with its transport in vesicles or via plasma membrane transporters. In particular, the demonstration of a sodium-dependent active transport of XA in cultured neurons represents a novel target for XA structural analogs, or more generally for synthetic ligands interfering with said transport system. In fact, inhibition of this transport system results in an increase in the half-life of XA in certain functional compartments of brain, in particular the synaptic compartment. Inhibitors of this transport thereby represent a novel class of substances having beneficial effects in several types of neurological or mental pathologies.

Another useful compound according to the invention is a compound modulating the synthesis, transport or activity of the XA receptor. Such compounds, by reducing or facilitating exposure of XA receptors, allow local modulation of the activity of this molecule.

Compounds modulating XA activity according to the invention may be of diverse nature and origin. They may be inorganic or organic products and notably a polypeptide (or a protein or a peptide), a nucleic acid, a lipid, a polysaccharide, a chemical or biological compound, and the like. The compound may be of natural or synthetic origin and in particular come from a combinatorial library. Preferably, such compounds are derivatives of xanthurenic acid or kynurenic acid.

The compounds or compositions of the invention may be administered in different ways and in different forms. For instance, they may be administered by the systemic or oral route, preferably systemically, such as for example by the intravenous, intramuscular, subcutaneous, transdermal, intra-arterial, intracerebral, intraperitoneal, intracerebrovascular route, etc. For injections, the compounds are generally prepared in the form of liquid suspensions, which may be injected through syringes or by infusion, for instance. In this respect, the compounds are generally dissolved in pharmaceutically compatible saline, physiologic, isotonic, buffered solutions and the like, known to those skilled in the art. For instance, the compositions may contain one or more agents or vehicles chosen from among dispersives, solubilizers, stabilizers, preservatives, and the like. Agents or vehicles that may be used in the liquid and/or injectable formulations comprise in particular methylcellulose, hydroxymethylcellulose, carboxymethylcellulose, polysorbate 80, mannitol, gelatin, lactose, vegetable oils, acacia, and the like. The compounds may also be administered in the form of gels, oils, tablets, suppositories, powders, capsules, gelules and the like, possibly by means of pharmaceutical forms or devices allowing sustained and/or delayed release. For this type of formulation, an agent such as cellulose, carbonates or starches is advantageously used.

It is understood that the injection rate and/or injected dose may be adapted by those skilled in the art according to the patient, the pathology, the mode of administration, etc. Typically, the compounds are administered at doses ranging from 0.1 μg to 1000 mg/kg of body weight, more generally from 0.01 to 500 mg/kg, typically between 1 and 200 mg/kg. Furthermore, repeated injections may be given, as the case may be. In addition, in the case of chronic treatments, delayed or sustained release systems may be advantageous.

As a rough guide, the results presented in the examples reveal that XA has a sedative effect when administered to animals at doses greater than approximately 50 mg/kg. The preferred doses to obtain an anxiolytic effect in animals are doses of less than 50 mg/kg. An antidepressant effect is advantageously obtained in animals at doses comprised between 100 and 200 mg/kg.

The invention also concerns methods to identify, select or characterize biologically active compounds, particularly compounds active on the nervous system, said methods being based on modulation of XA activity. The inventive methods may comprise in vitro binding tests, binding tests in cell systems (or on natural or synthetic membrane preparations) or functional tests in cell or artificial systems.

According to a particular embodiment, a method for selecting, identifying or characterizing compounds according to the invention comprises contacting a test compound with a cell (or a natural or synthetic membrane preparation)

expressing a target molecule involved in xanthurenic acid activity, and demonstrating a binding of the test compound to said target.

The target molecule may be the XA receptor, an XA synthetic enzyme, an XA transporter, etc., or any fragment thereof. In a specific example, the target molecule is the XA receptor or a fragment thereof, particularly a fragment conserving the ability to bind XA, such as for instance an extracellular fragment. In another embodiment, the target molecule is an enzyme involved in XA biosynthesis or regulation, such as for example kynurenin-3-hydroxylase. A preferred target molecule is represented by the XA receptor or fragments thereof.

The binding of the test compound to the target molecule may be demonstrated for example by using a labelled test compound or by using a labelled ligand of the target molecule (for example a labelled XA receptor ligand or a labelled antibody specific of an XA synthetic enzyme or an XA transporter), displacement of the binding of the labelled ligand reflecting the binding of the test compound. The labelled ligand may be any product which binds the target molecule (antibody, agonist or antagonist, fragment or derivative of an endogenous ligand, etc.). The ligand may be labelled by any method known to those skilled in the art, particularly by incorporation of a radioactive, fluorescent, luminescent, enzymatic, colorimetric moiety, etc.

In a particular embodiment, the ligand is a labelled antibody, specific of the target molecule under study. The antibody may be polyclonal or monoclonal. It may also be an antibody derivative or fragment, such as for example the Fab, Fab'2, CDR fragments, etc. The antibodies may be produced by conventional means, by immunizing the target molecule (or an immunogenic part thereof) and recovering serum (polyclonal) or spleen cells (for hybridoma production through fusion with an appropriate line), such as described for example in Vaitukaitis et al. (J. Clin. Endocrinol. Metab. 1971, 33(6): 988–91) or in Harlow et al. (Antibodies: A Laboratory Manual, CSH Press, 1988). The Fab or F(ab')2 fragments may be produced for example as described in Riechmann et al., 1988, Nature 332, 323–327.

In another particular embodiment, the target molecule is the XA receptor and the ligand is an endogenous ligand, an agonist or an antagonist of the receptor, which is labelled. In a specific embodiment, labelled XA, particularly radiolabelled, in particular tritiated, is used.

According to a particular embodiment, the method therefore comprises contacting a test compound with a cell (or a natural or synthetic membrane preparation) expressing a xanthurenic acid receptor and demonstrating a binding of the test compound to the receptor.

According to another particular embodiment, the method comprises contacting a test compound with a cell (or a natural or synthetic membrane preparation) expressing a target molecule involved in xanthurenic acid activity, in the presence of a labelled ligand of said target, and demonstrating a binding of the test compound by measuring the displacement of binding of the labelled ligand.

In a further variant, the method of the invention comprises contacting a test compound with a cell expressing a target molecule involved in xanthurenic acid activity (in particular the xanthurenic acid receptor), and demonstrating a biological or pharmacological effect characteristic of a binding of the test compound to said target molecule. The biological or pharmacological effect may be the expression of one or more cellular proteins, the expression of a receptor, the activation of a gene, the endocytosis of the receptor, the appearance of an electrical current, a flux or influx of ions, etc. Such effect may be demonstrated by any suitable means, such as measuring the expression of a reporter gene, measuring the membrane expression of a receptor, assaying ions or electrical current, and the like.

Classically, the effect of the test compound is compared to the effect determined in the absence of said compound. Furthermore, the effect of the test compound may be determined in the presence of an XA receptor ligand, for example XA itself, particularly when an XA modulating or inhibiting activity is sought.

According to a particular variant, the method of the invention therefore comprises contacting a test compound with a cell expressing a xanthurenic acid receptor, in the presence of a ligand of said receptor, measuring a biological or pharmacological effect characteristic of a binding to the XA receptor and comparing the effect so measured with that obtained in the absence of the test compound. Such method is especially suited to the research, selection, characterization or improvement of compounds that inhibit XA activity.

The cells used in the tests may be any cells expressing a target molecule involved in XA activity, particularly an XA receptor. They may be cells naturally expressing this molecule (e.g., this receptor), or cells genetically modified or treated so as to overexpress said molecule (e.g., said receptor). In a preferred embodiment of the invention, they are mammalian cells (nerve cells, hepatocytes, fibroblasts, endothelial, muscle cells, etc.). Even more preferably, such cells are human cells. They may also be primary cell cultures or established cell lines. In another embodiment, it is also possible to use prokaryotic cells (bacteria), yeast cells (Saccharomyces, Kluyveromyces, etc.), plant cells, and the like.

In a preferred embodiment, nerve or synaptic cells are used, particularly neurons, glial cells, astrocytes, material of synaptic origin (membranes, synaptosomes, synaptoneurosomes), etc. Such cells may be isolated, cultured and characterized according to known methods, described in the examples.

The invention demonstrates, for the first time, the existence of a high affinity receptor for XA expressed in different cell populations or regions of the brain. Said receptor has the following pharmacological features:
  expression in brain,
  $K_d$ of the synaptic XA receptor less than or equal to approximately 300 nM to 1300 nM,
  receptor modulated by adenylate derivatives (adenosine, ADP, ATP)
  receptor modulated by copper and zinc ions,
  receptor modulated by kynurenic acid,
  receptor activation by XA induces an electrical current,
  receptor expressed by NCB-20 cells.

Moreover, electrophysiological and biochemical data suggest a receptor coupled to G proteins, although this has not been formally demonstrated.

The characterization of this receptor, its identification and the description of the methods whereby to measure the binding of molecules to said receptor, according to this application, make it possible to demonstrate novel biologically active compounds, capable of modulating XA activity. The demonstration of the pharmacological role of XA emphasizes the importance of making such active compounds available.

In a particular embodiment, the hereinabove methods are carried out by using a membrane preparation expressing an XA receptor. In an advantageous manner, the membrane preparation is of natural origin, that is to say, produced from a cell expressing the receptor. Membrane preparations may be produced by mechanical, chemical, physical, electrical lysis, etc. and in particular by treatment with detergents, ultrasound, freeze/thaw, etc., as illustrated in the examples. Such membrane preparation is characterized primarily by the presence of membrane fragments, containing a lipid bilayer in which all or part of the XA receptor is present. Such membrane preparations are generally devoid of intact cells. Furthermore, they may be enriched in membrane debris by suitable treatments (centrifugation, etc.). A membrane preparation of synthetic origin may also be used, such as for example a liposome in which all or part of the XA receptor has been inserted, or a supported membrane.

For the binding or functional tests hereinabove, the compounds may be contacted with the cells (or membrane preparations) at different times, depending on their effect(s), their concentration or the type of cell and for different periods, which may be adapted by those skilled in the art. The test may be carried out on any suitable support and particularly on a plate, slide, dish, in a tube or flask. Generally the contact is done in a multiwell plate which makes it possible to simultaneously conduct numerous and diverse tests. Typical supports include microtitration plates and more particularly plates with 96 or 384 wells (or more), which are easy to manipulate.

Depending upon the support and the nature of the test compound, variable amounts of cells may be used when carrying out the described methods. Classically, $10^2$ to $10^6$ cells are contacted with a type of test compound, in a suitable culture medium, and preferably between $10^3$ and $10^5$ cells. When a membrane preparation is used, 0.01 to 50 mg per protein per test is generally used, more preferably from 0.05 to 2 mg of protein per test. The tests may be carried out in any suitable medium, such as for example saline solutions, buffers, etc. Specific examples of buffers include Tris, Pipes, Hepes, etc. The temperature is typically close to room temperature. The pH of the medium is advantageously comprised between 5.5 and 8, more preferably between 7 and 8. It is understood that these parameters may be adapted by those skilled in the art, following the indications given in the examples.

The quantity (or concentration) of test compound may also be adjusted by the user according to the type of compound (its toxicity, ability to penetrate cells, etc.), the incubation time, etc. Generally, the cells (or membranes) are exposed to quantities of test compound ranging from 1 nM to 1 mM. Of course other concentrations may be tested without deviating from the invention. Each compound may, furthermore, be tested in parallel, at different concentrations and for different times. Moreover, adjuvants and/or vectors and/or products facilitating penetration of the compounds into the cells such as liposomes, cationic lipids, polymers, viral peptides, etc. may additionally be used, where necessary. Contact may be maintained for a period comprised between 1 minute and several hours, according to the nature of the target molecule. When the target molecule is the XA receptor, contact is typically for less than approximately 1 hour. When the target molecule is an intracellular molecule, contact may be maintained for a longer time.

In another variant, the invention is based on in vitro binding tests between XA and a test compound or between a test compound and a target molecule (for example all or part of the XA receptor). According to such embodiments, the method by which to select, identify or characterize active compounds comprises:
  contacting a test compound with a target molecule involved in XA activity, for example a synthesis or regulatory enzyme, a transporter, a receptor, or a fragment thereof, and
- determining the possible binding of said test compound to said molecule.

Binding of the test compound may be demonstrated in different ways, such as for example by gel migration or electrophoresis of the complexes formed. Other methods based on luminescence or the FRET (Fluorescence Resonance Energy Transfer) method familiar to those skilled in the art or the SPA (Scintillation Proximity Assay) method, may be used, within the scope of the present invention, to determine the possible binding of the test compound to the target molecule. When the target is a receptor, binding may be measured in the presence of a labelled ligand, by measuring displacement of the ligand by the test compound.

The present invention may be applied to any type of test compound. For instance, the test compound may be any product alone or mixed with other products. The compound may be defined in terms of its structure and/or composition or it may not be defined. The compound may, for example, be an isolated and structurally defined product, an isolated product of undefined structure, a mixture of known and characterized products or an undefined composition comprising one or more products. For example, such undefined compositions may be samples of tissue, biological fluids, cellular supernatants, plant preparations, etc. The test compounds may be inorganic or organic products and particularly a polypeptide (or a protein or a peptide), a nucleic acid, a lipid, a polysaccharide, a chemical or biological compound such as a nuclear factor, a cofactor or any mixture or derivative thereof. The compound may be natural or synthetic and include a combinatorial library, a clone or a library of nucleic acid clones expressing one or more DNA-binding polypeptide(s), etc.

Another object of the invention relates to a method for producing an active compound, particularly on the nervous system, the method comprising:

- determining the ability of a compound to modulate XA activity in vitro or ex vivo, and
- synthesizing said compound or a structural analog thereof.

Another object of the invention concerns a method for producing a modulator of XA, the method comprising:

- contacting a compound with a target molecule involved in XA activation,
- determining the effect of the compound on the target molecule, said effect indicating that the compound is a modulator of XA, and
- synthesizing said compound or a structural analog thereof.

A further object of the invention concerns a method for producing a medicament comprising an active compound, particularly on the nervous system, the method comprising:

- determining the ability of a compound to modulate XA activity in vitro or ex vivo, and
- combining said compound or a structural analog thereof with a pharmaceutically acceptable vehicle.

Another object of the invention concerns a method for producing a medicament comprising an XA modulator compound, the method comprising:

- contacting a compound with a target molecule involved in XA activation,
- determining an effect of the compound on the target molecule, said effect indicating that the compound is a modulator of XA, and
- combining said compound or a structural analog thereof with a pharmaceutically acceptable vehicle.

Within the scope of the invention, the term "structural analog" denotes any molecule obtained by molecular modelling or structural variation from a test compound.

Other advantages and aspects of the invention will become apparent in the following examples, which are given for purposes of illustration and not by way of limitation.

LEGENDS OF FIGURES

FIG. 1: Extracellular concentration of XA in the prefrontal cortex (PFC)

Figures 2A, 2B:
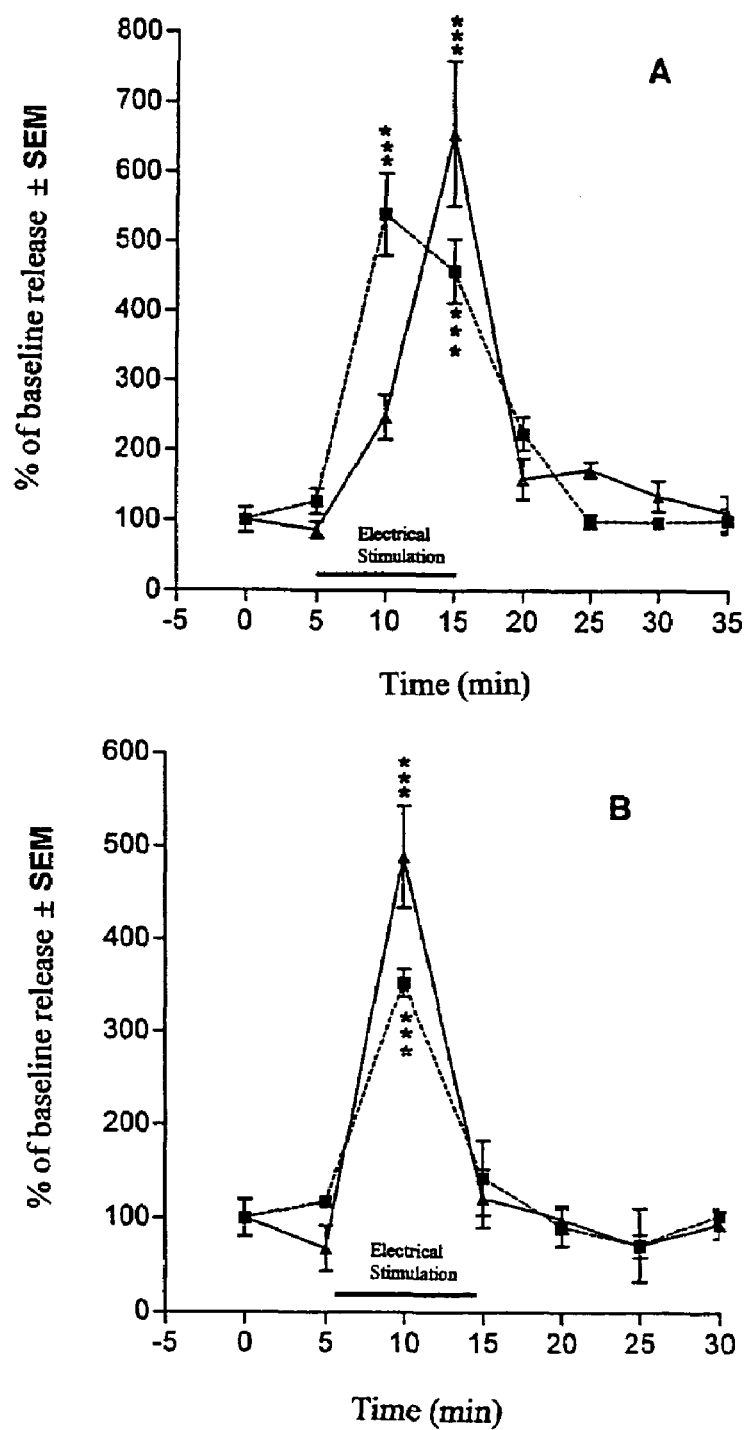

FIGS. 2A and 2B: XA release in the PFC after electrical stimulation of the VrA (FIG. 2A=100 µA; FIG. 2B=200 µA). Dopamine=black triangles; XA=black squares FIG. 3: XA release induced by 100 mM KCl in the probe for 5 min.

Figure 4:
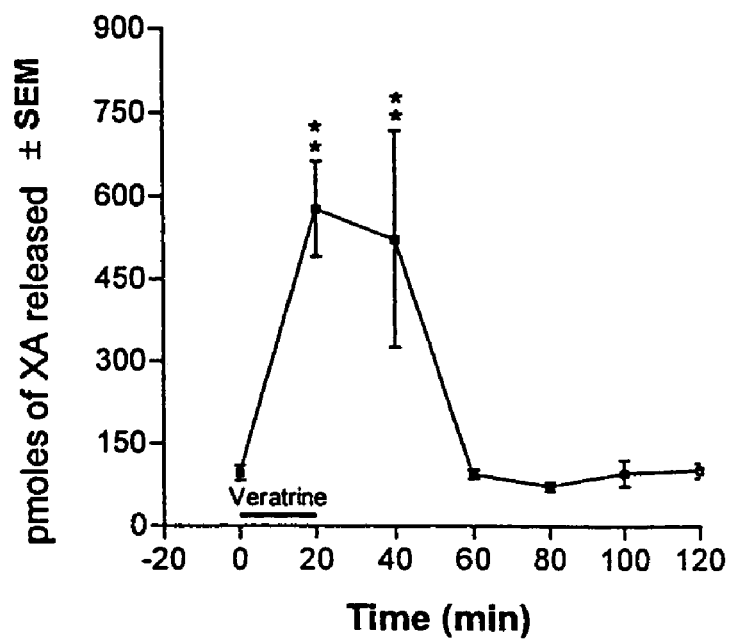

FIG. 4: XA release induced by 50 µM veratridine in the probe for 20 minutes.

Figure 5:
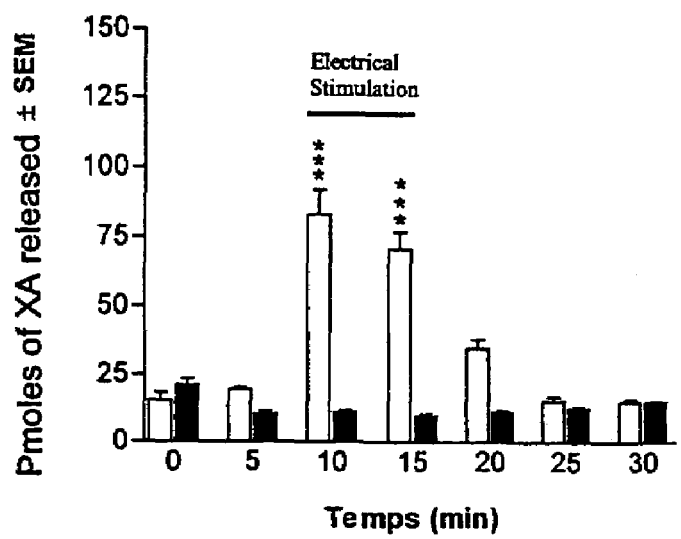

FIG. 5: XA release in the PFC after electrical stimulation (white bars). The same experiment in the absence of calcium ions and in the presence of EGTA shows that XA release is no longer increased after electrical stimulation (black bars).

Figure 6:
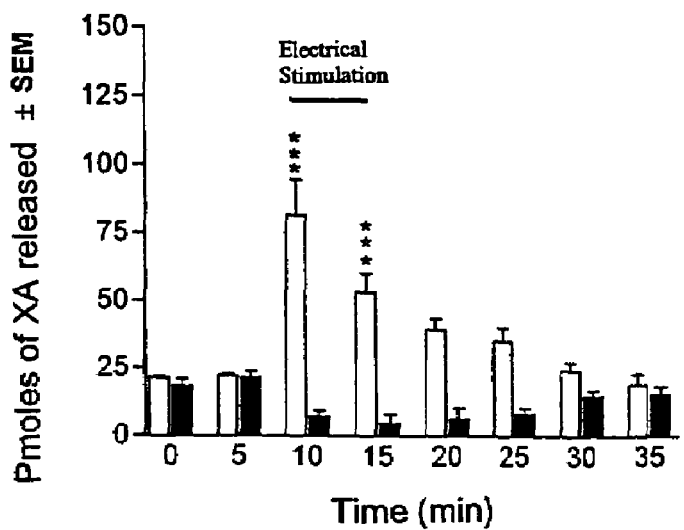

FIG. 6: XA release in the PFC after electrical stimulation of the VTA (white bars, baseline=21 pmol/5 min). Same experiment but with 2.0 µM TTX in the dialysis medium (black bars, baseline=7 pmol/5 min). In the presence of TTX, electrically-induced XA release is blocked.

Figure 7:
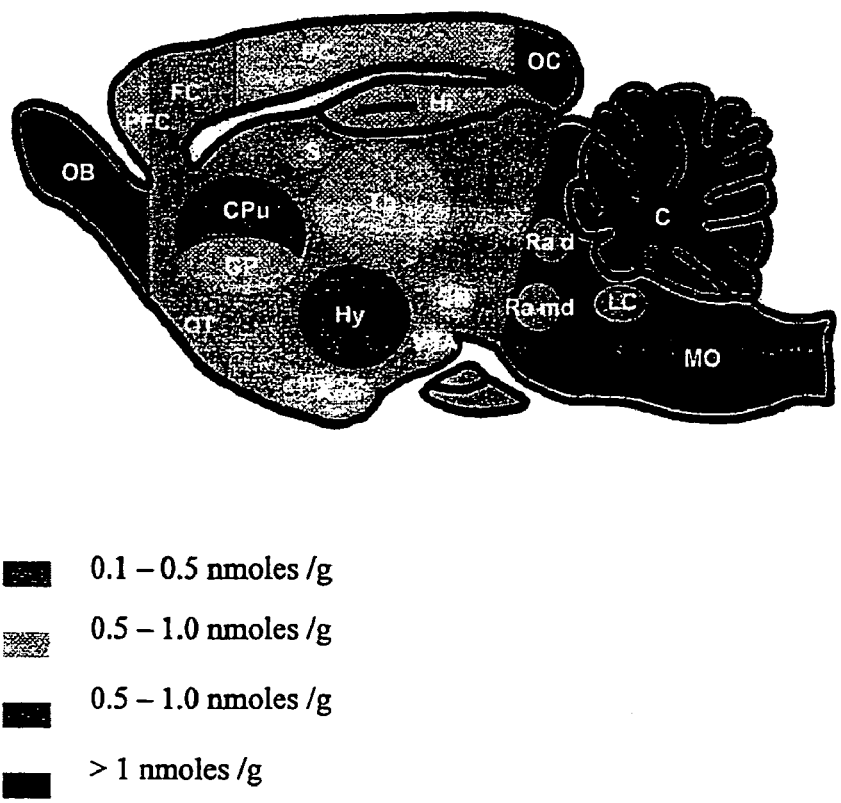

FIG. 7: Distribution of XA in rat brain under physiological conditions. Concentrations are arbitrarily color coded. Abbreviations: PFC: prefrontal cortex; FC: frontal cortex; PC: parietal cortex; OC: occipital cortex; C: cerebellum; GP: globus pallidus; CPu: caudate putamen; n.Acc: nucleus accumbens; OT: olfactive tubercules; OB: olfactive bulbs; S: septum; Hb: habenula; Hi: hippocampus; Th: thalamus; Hy: hypothalamus; SN: substantia nigra (A9); VTA: ventral tegmental area (A10); Rad: dorsal raphe nucleus; Ram: median raphe nucleus; LC: locus caeruleus (A6); MO: medulla oblongata.

Figure 8:
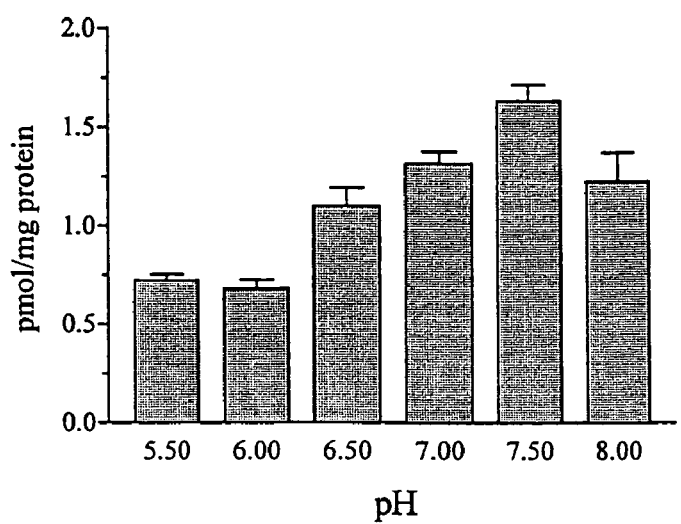

FIG. 8: Effect of pH on XA binding to its binding site(s).

Figure 9:
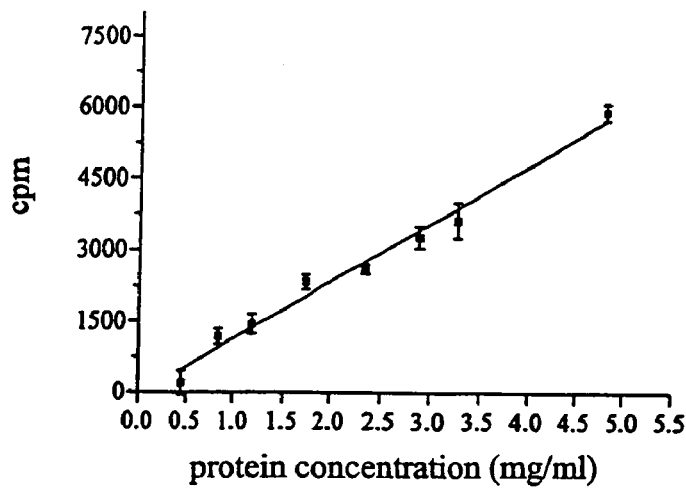

FIG. 9: Linearity study of specific binding according to protein concentration.

Figure 10:
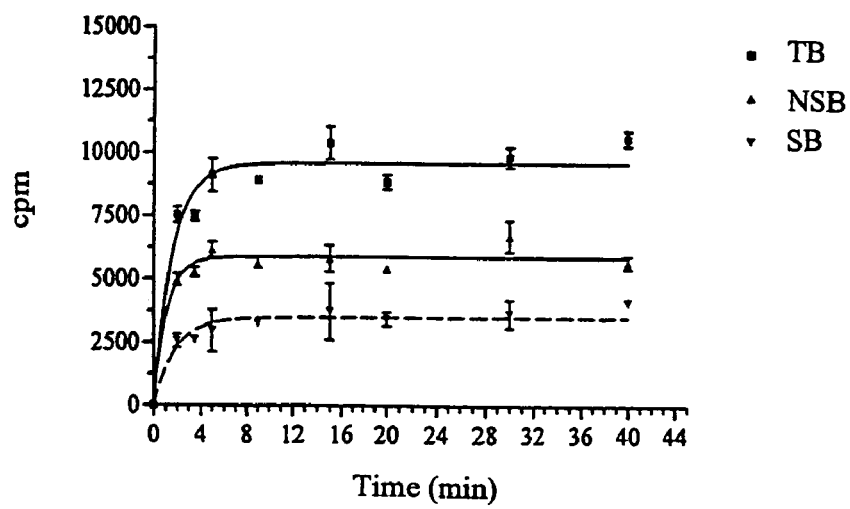

FIG. 10: Determination of association constant $K_{on}$

Figure 11:
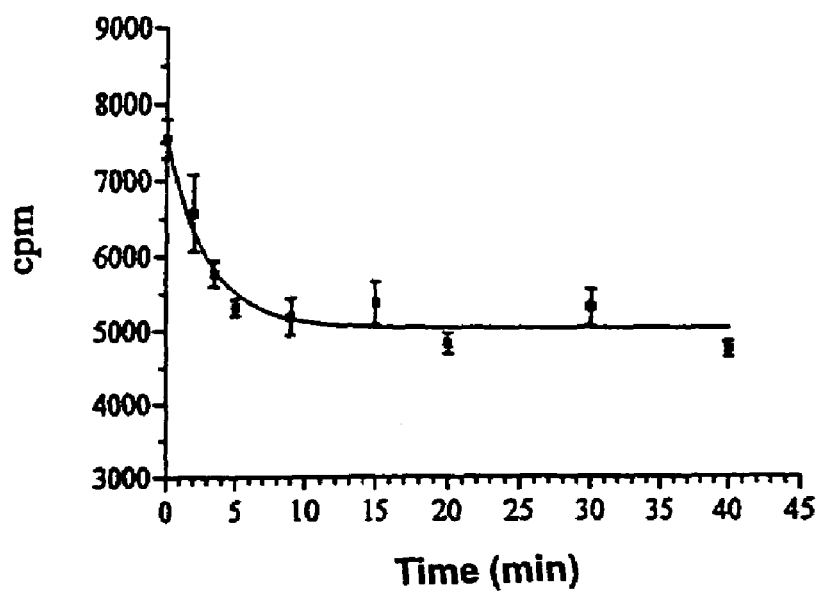

FIG. 11: Determination of dissociation constant $K_{off}$

Figure 12:
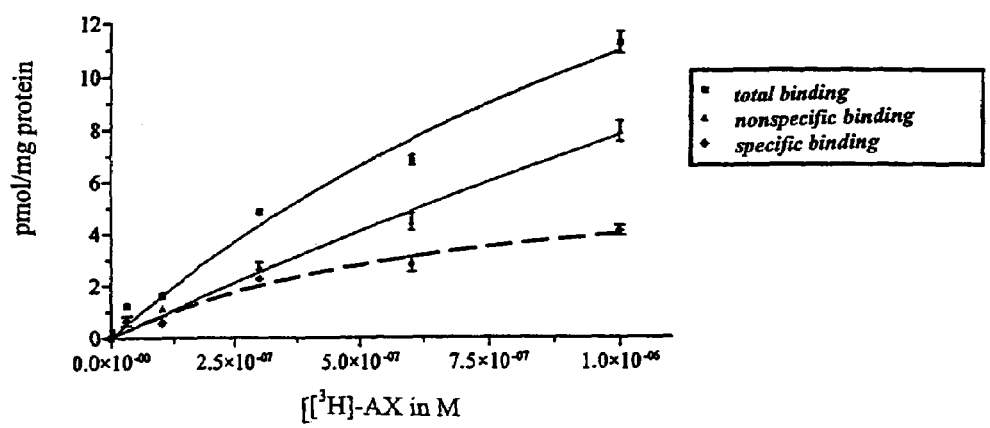

FIG. 12: Saturation curve of XA membrane sites. Determination of $K_d$ and $B_{max}$.

Figure 13:
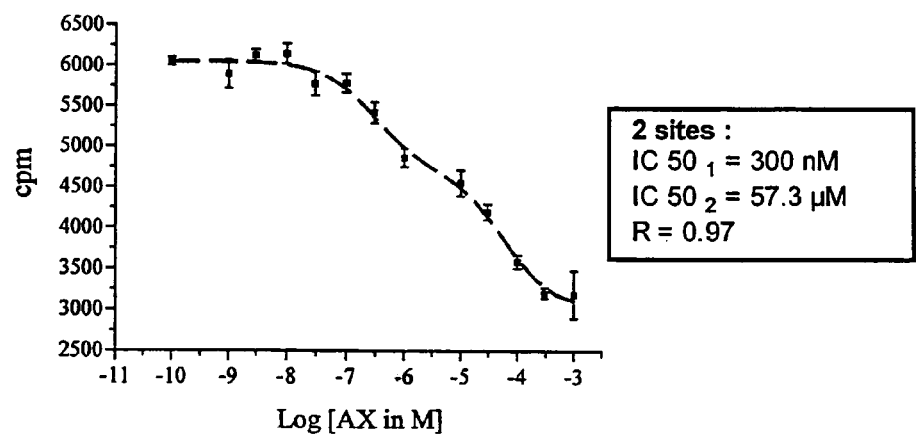

FIG. 13: Competitive inhibition of radiolabelled XA binding by non-radiolabelled XA. Determination of $IC_{50}$ for xanthurenic acid.

Figure 14:
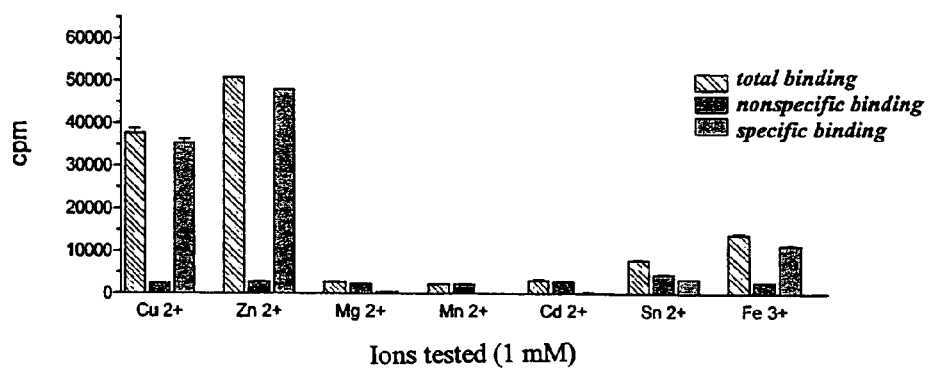

FIG. 14: Effect of metal ions on xanthurenic acid binding to its binding site(s).

Figure 15:
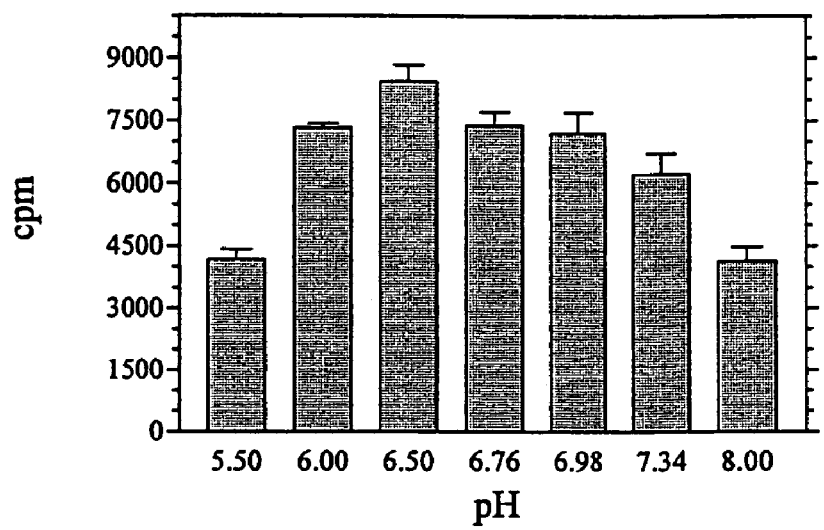

FIG. 15: Effect of pH on XA binding to its binding site(s) in the presence of copper ions.

Figure 16:
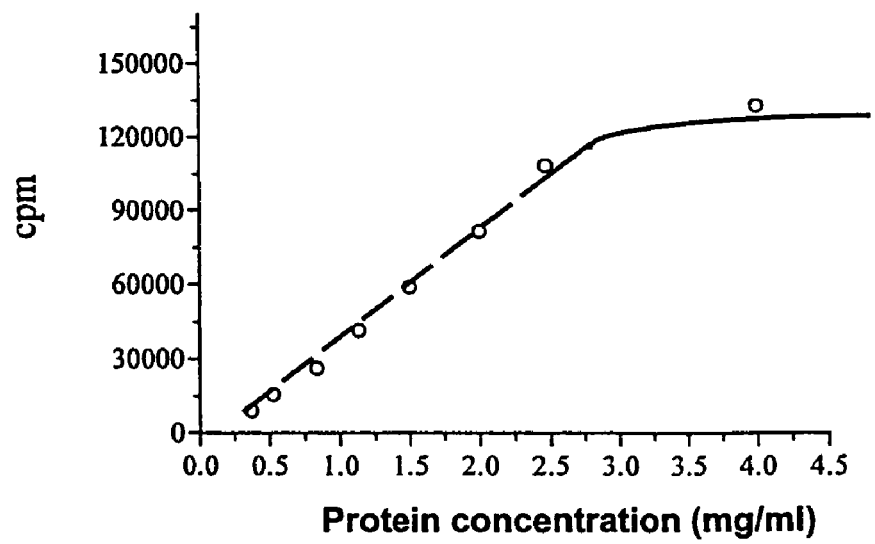

FIG. 16: Linearity study of specific binding according to protein concentration in the presence of copper ions.

Figure 17:
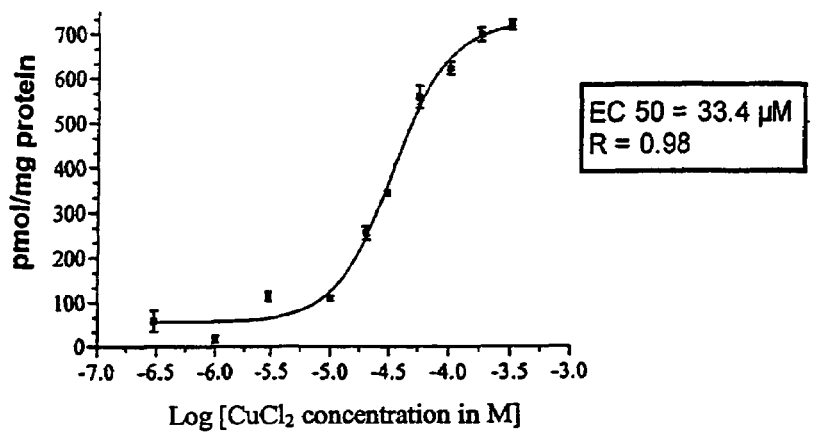

FIG. 17: Dose-effect of copper ($Cu^{2+}$) on XA binding to its binding site(s).

Figure 18:
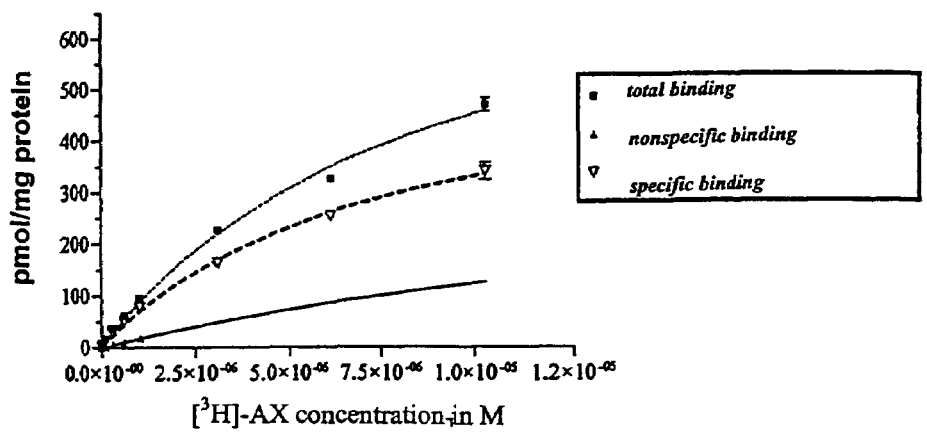

FIG. 18: Saturation curve and $K_d$ and $B_{max}$ determination in the presence of copper ions.

Figure 19:
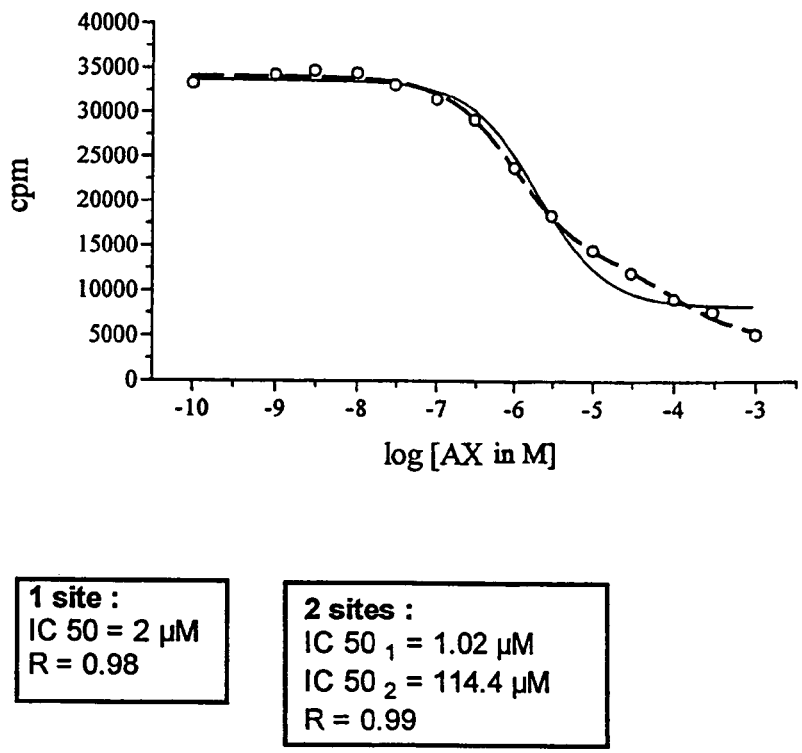

FIG. 19: Competitive inhibition of radiolabelled XA binding by non-radiolabelled XA. Determination of $IC_{50}$ for xanthurenic acid.

Figure 20:
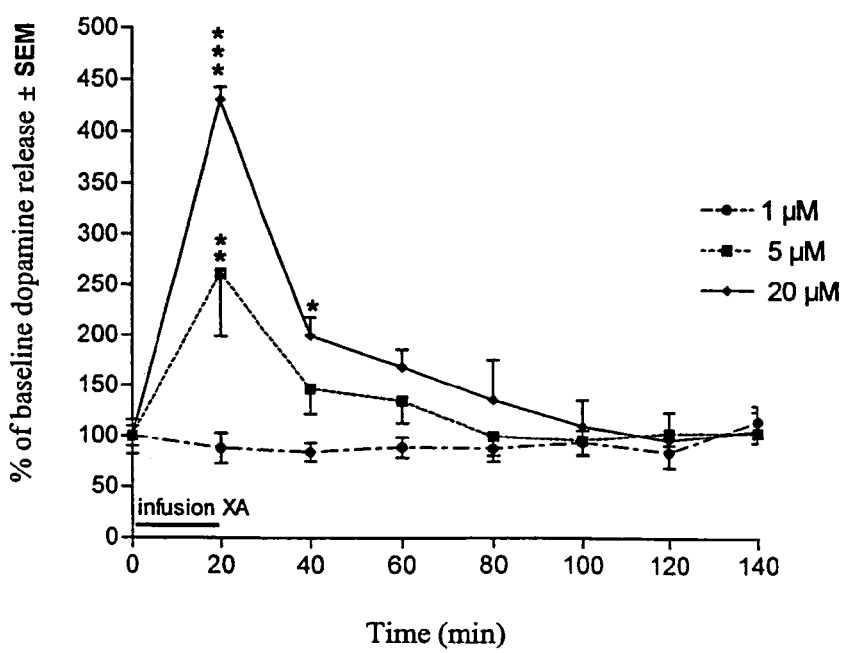

FIG. 20: Dose/effect of XA on the dopaminergic response after local injection in the PFC.

Figure 21:
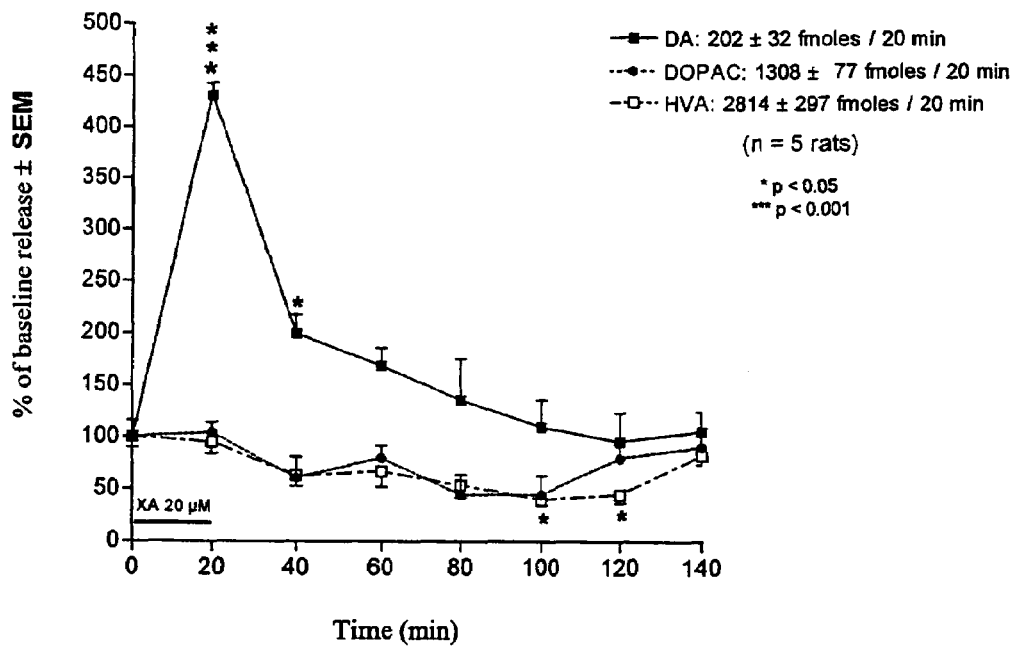

FIG. 21: Variations in dopamine, DOPAC and HVA release in the PFC after local application of 20 µM XA.

Figure 22:
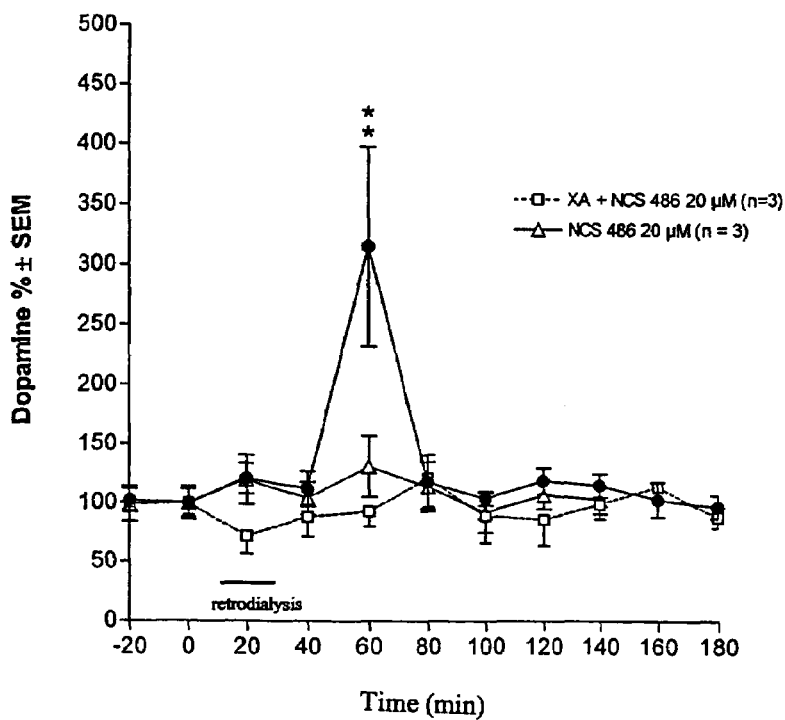

FIG. 22: Effects of the antagonist NCS-486 on extracellular dopamine release after local application of 20 µM XA in the PFC.

Figure 23:
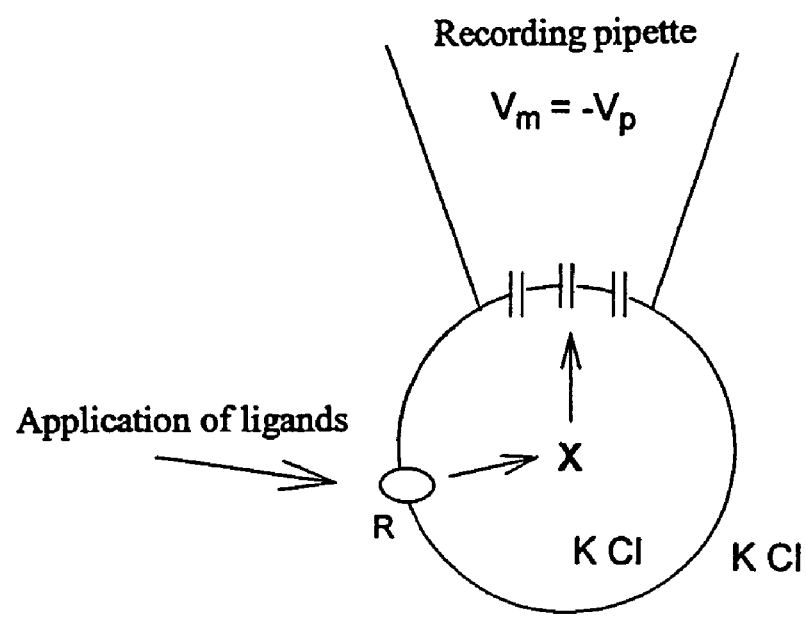

FIG. 23: Experimental configuration of patch-clamp studies.

Figure 24:
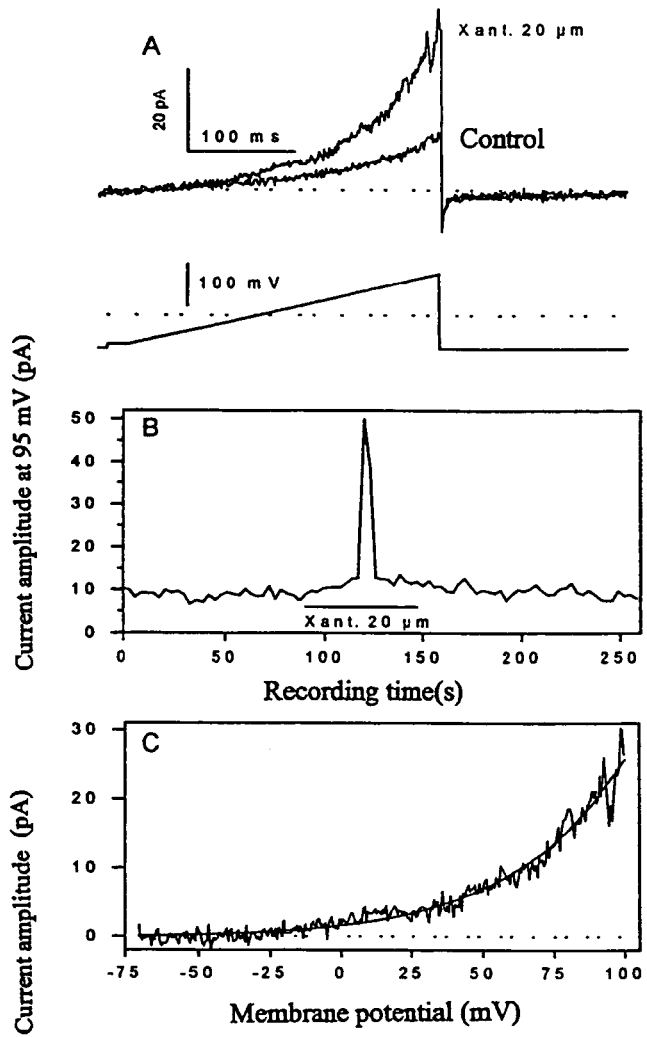

FIG. 24: Effect of xanthurenic acid on NCB-20 cells.
  A. Sample traces recorded on a membrane fragment under control conditions and during application of 20 µM xanthurenic acid. The membrane fragment was stimulated by a potential ramp as indicated in the protocol shown in the lower trace. In the presence of xanthurenic acid a large outflux current develops at positive potentials. The trace was digitized at a frequency of 2 kHz.
  B. Variations in the mean outflux current measured at a potential of 95 mV. In the presence of xanthurenic acid this current is considerably increased.
  C. Current-potential relationship of the active current in the presence of xanthurenic acid (after subtracting the current observed in control condition). The solid line fits this current to the Boltzmann model.

Figure 25:
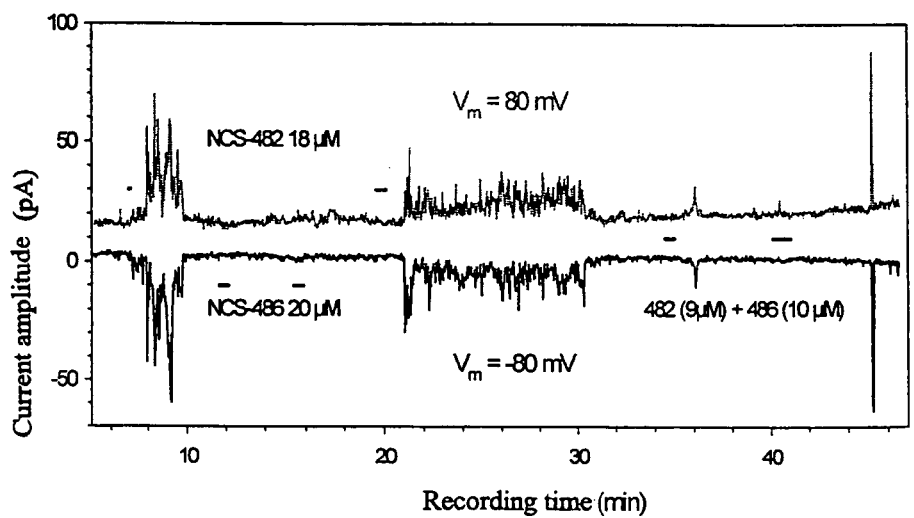

FIG. 25. Pharmacology of the response to xanthurenic acid. The membrane current measured at potentials of −80 and 80 mV is plotted against recording time. Solid lines indicate the incubation periods of the xanthurenate receptor ligands: upper and lower respectively for NCS-482 and NCS-486 alone and middle for the mixture of the two at the indicated concentrations. NCS-482 and NCS-486 are xanthurenic acid derivatives. NCS-486 alone does not change the current amplitude.

Figure 26:
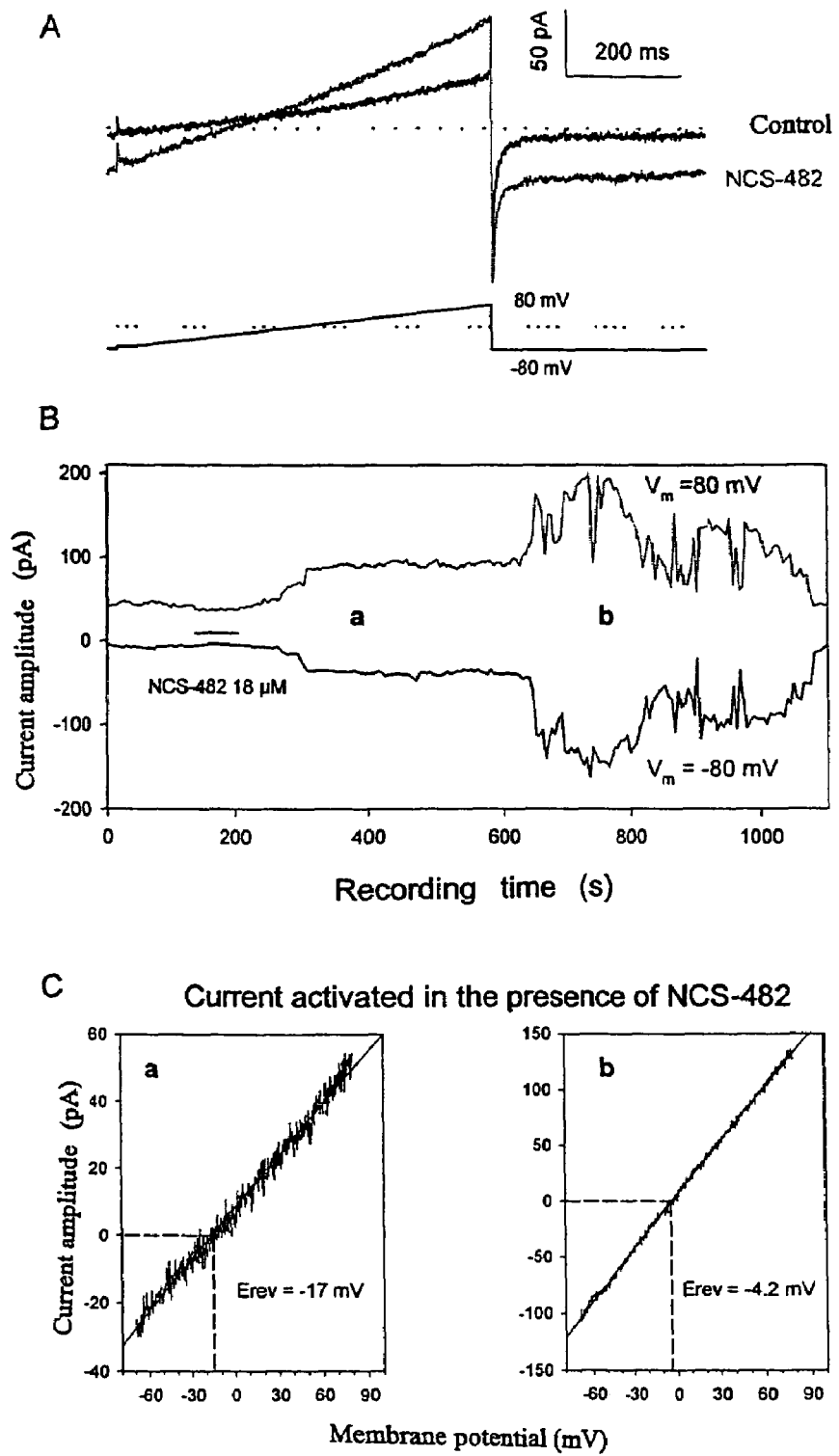

FIG. 26: Activation of chloride conductance by the xanthurenic acid receptor. The agonist used in this experiment is NCS-482 at 20 µM concentration. The response develops in two phases (a and b). The nature of the current in these two phases differs as shown by the inversion potential of the current obtained in each of the two phases (lower panels).

Figure 27:
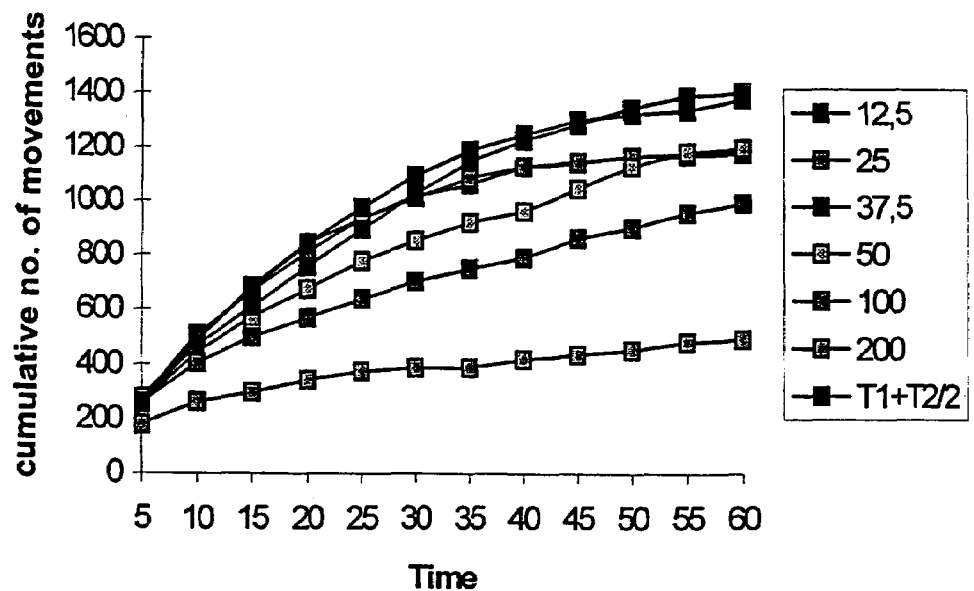

FIG. 27: Spontaneous locomotor activity of animals treated with increasing doses of XA. Time is given in minutes.

Figure 28:
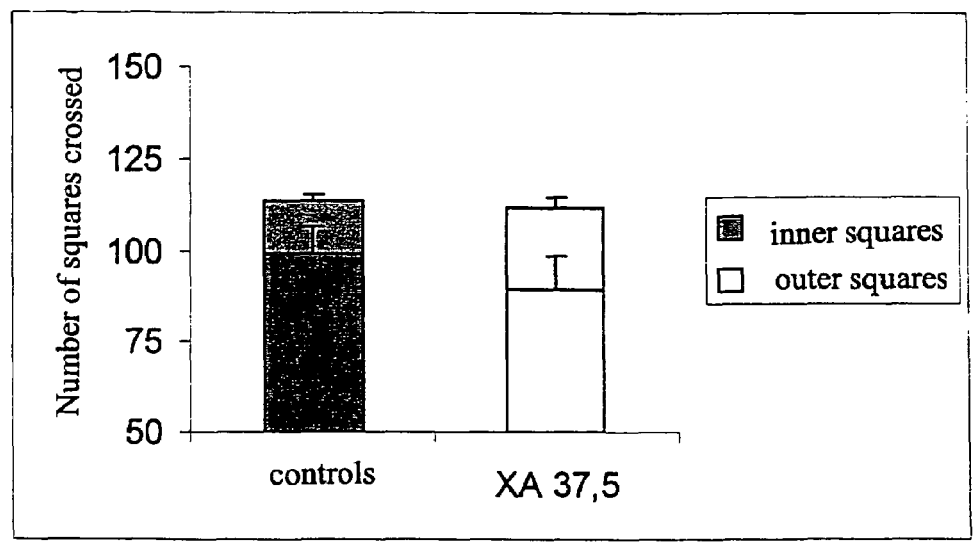

FIG. 28: Global reactivity of animals in the open field test. XA at a dose of 37.5 mg/kg (non-sedative dose) promotes movement of the animal to the center of the lighted open field as compared to control animals.

Figure 29:
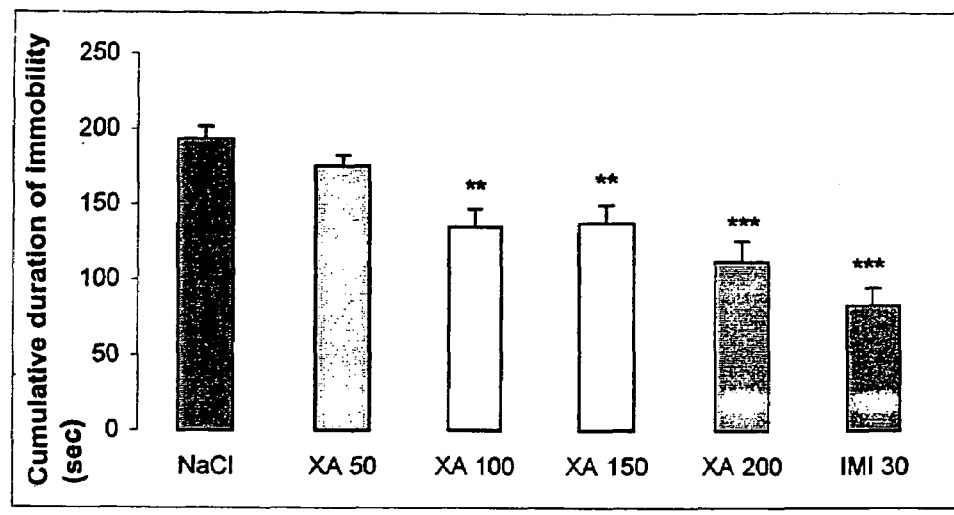

FIG. 29: Dose/effect of XA in the Porsolt test (swimming test). The duration of immobility decreases with increasing doses of XA. Rats treated with imipramine 30 mg/kg served as positive controls.

Figure 30:
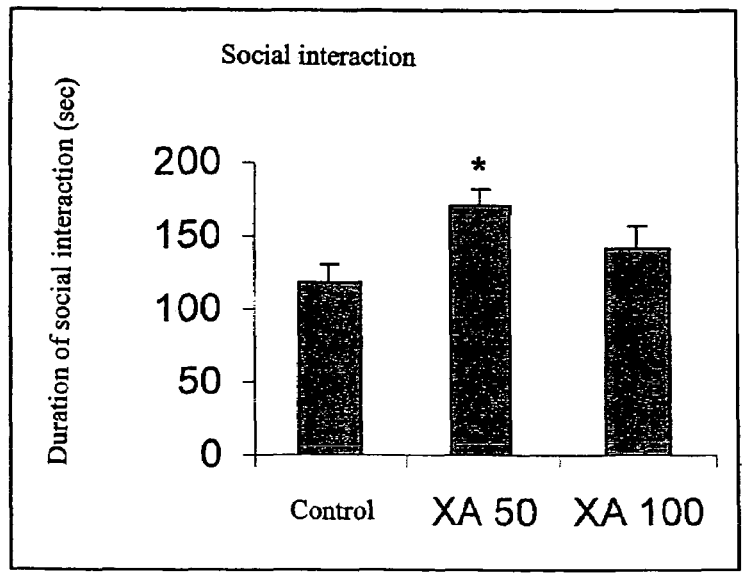

FIG. 30: In the open field test, an XA dose of 50 mg/kg induces an increase in the duration of social interactions compared to untreated animals. This result also suggests that XA has an anxiolytic effect.

Figure 31:
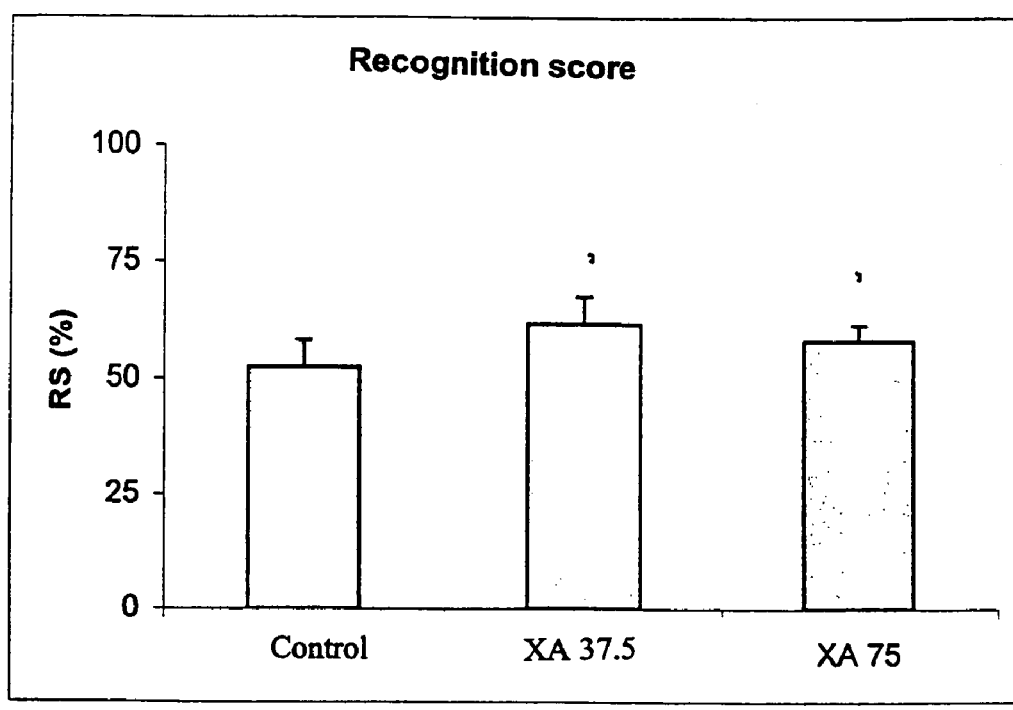

FIG. 31: Effect of XA on memorization processes in the object recognition test.

Figure 32:
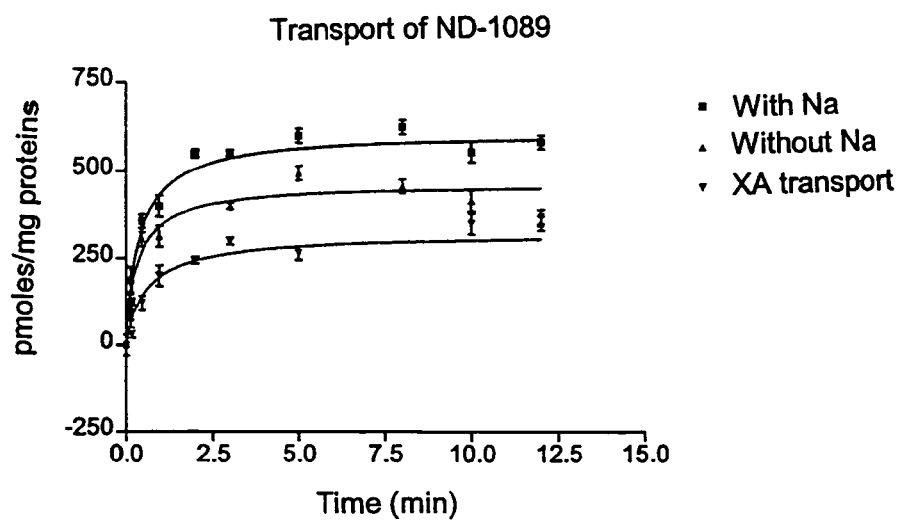

FIG. 32: Transport kinetics of XA (ND-1089) in NCB-20 cells. The maximal transport velocity is reached after approximately 1 minute.

Figure 33:
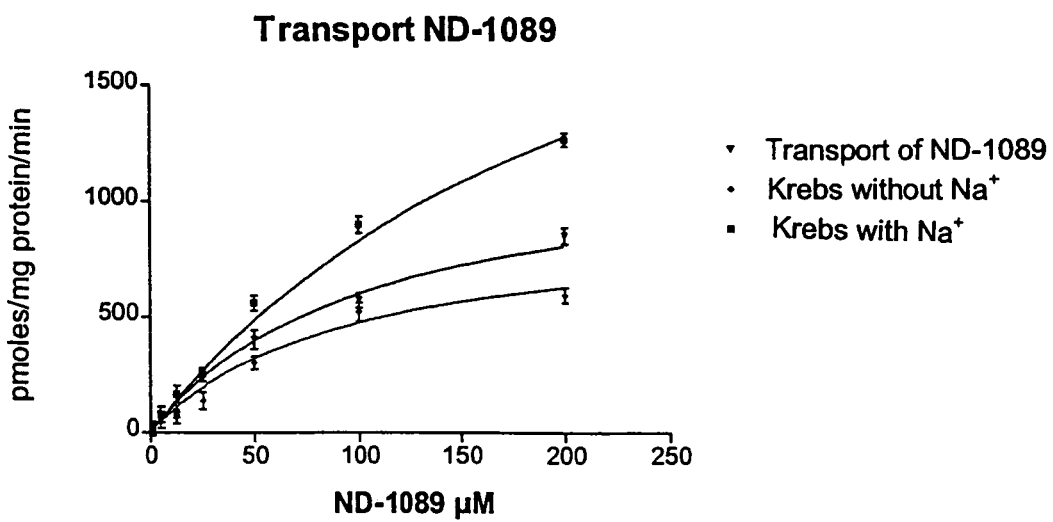

FIG. 33: XA (ND-1089) transport in NCB-20 cells according to [$^3$H]-XA concentration. The Scatchard plot allows determination of the mathematical constants of intracellular transport of ND-1089: $K_m$=105 µM and $V_{max}$=1229 pmol/mg protein/minute.

Figure 34:
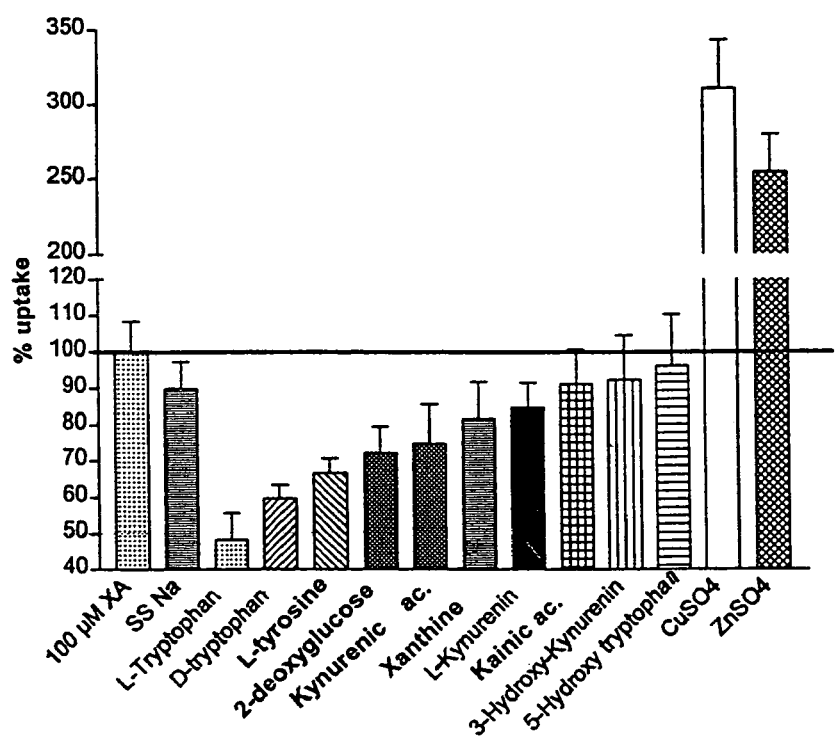

FIG. 34: Histogram showing the percentage uptake relative to transport in the presence of radiolabelled XA alone (=100%).

Figure 35:
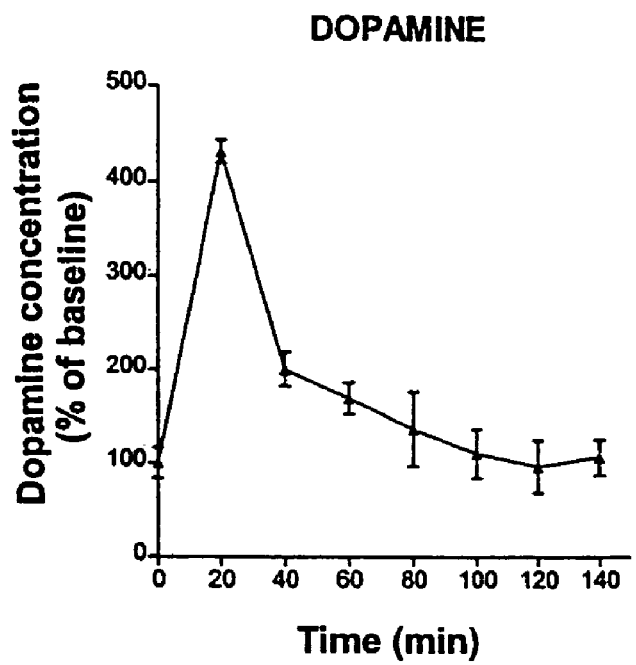

FIG. 35: Frontal extracellular release after retrodialysis of 20 µM XA for 20 minutes expressed as dopamine concentration in the dialysates (% of baseline) versus time (minutes).

Figure 36:
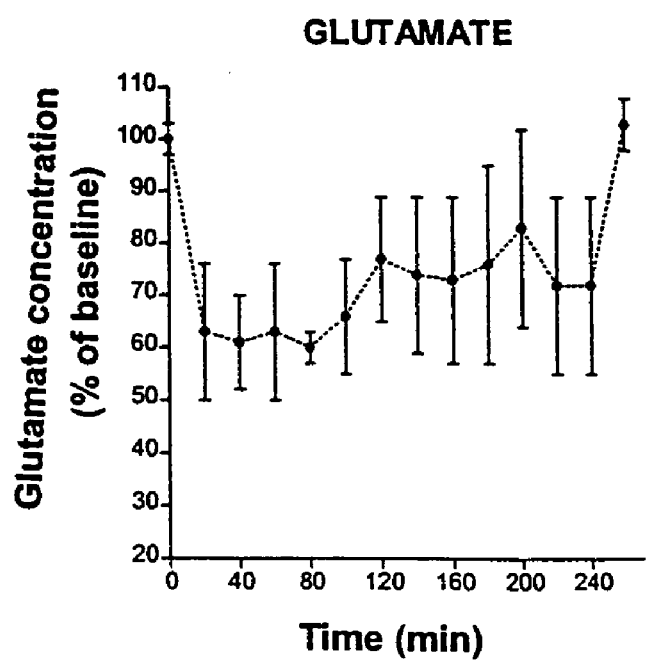

FIG. 36: Frontal extracellular release after retrodialysis of 20 µM XA for 20 minutes expressed as glutamate concentration in the dialysates (% of baseline) versus time (minutes).

Figure 37:
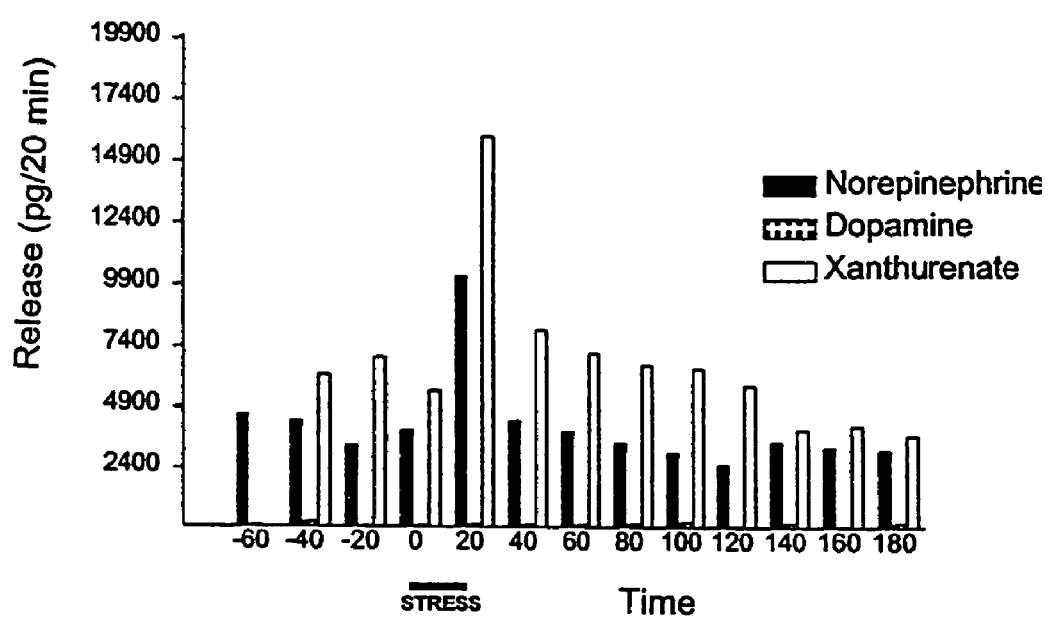

FIG. 37: Frontal extracellular release after retrodialysis of 20 µM XA for 20 minutes expressed as glutamate concentration (% of baseline) versus time (minutes).

Figure 38:
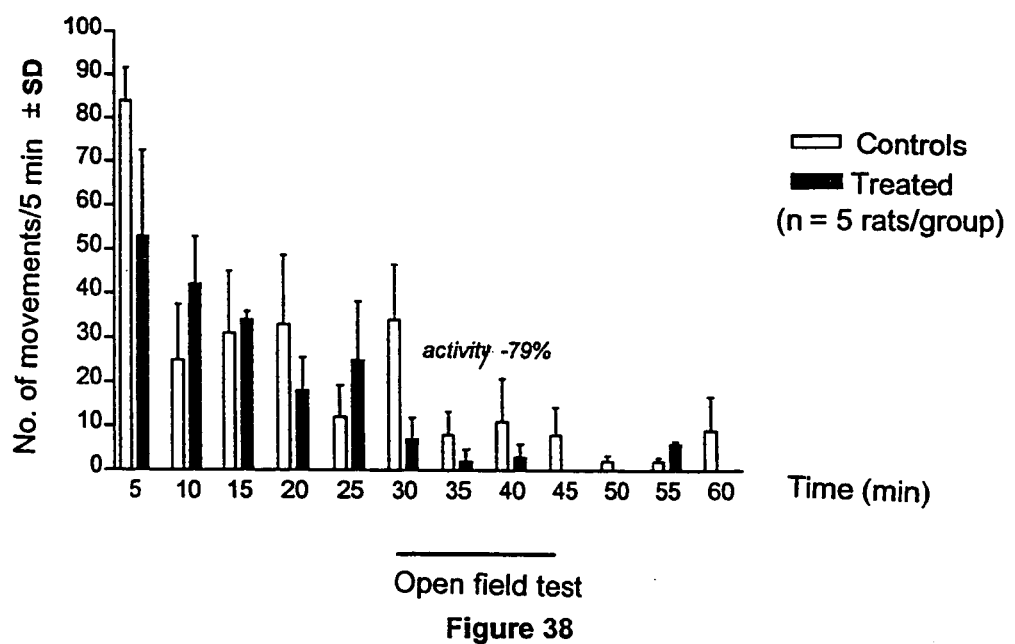

FIG. 38: Actograph obtained after administration of a xanthurenic acid derivative ligand named ND-7000, which binds to the allosteric site for kynurenic acid, an integral part of the XA receptor, at a dose of 100 mg/kg per os.

Figure 39:
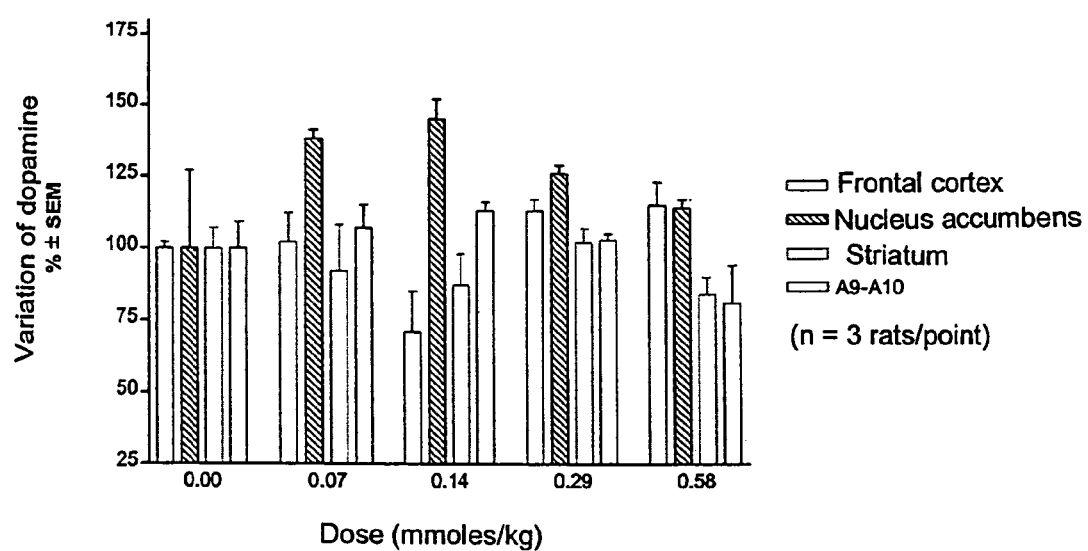

FIG. 39: Dose/response after p.o. administration of an XA receptor agonist—a xanthurenic acid derivative named ND-1301—on dopamine tissue levels in different parts of the brain.

EXPERIMENTAL SECTION

1. Demonstration and Characteristics of Extracellular Release of Xanthurenic Acid (XA) In Vivo in Rat Prefrontal Cortex.

Through a combination of electrical stimulation of the ventral tegmental area ($A_{10}$) and in vivo microdialysis in the prefrontal cortex in rats, extracellular release of XA could be demonstrated. This release can be reproduced by local depolarization induced by high potassium ion concentrations or micromolar quantities of veratridine. XA release is calcium-dependent and is blocked by tetrodotoxin which prevents local depolarization of neurons. XA is therefore released in this region of the brain at least, with characteristics identical to those of other known neurotransmitters, that is to say, according to an exocytotic mechanism induced by neuron depolarization.

Materials and Methods

Animals

Male Wistar rats weighing 350–400 g were used for the experiments. Animals were housed individually in plastic cages with a light/dark cycle of 7 a.m./7 p.m. and 7 p.m./7 a.m. Animals had access to food and water ad libitum. Animal experiments were conducted in strict accordance with the requirements of the European Directive of 24 Nov. 1986 (86/609/EEC).

Surgical Procedure

The experiments were carried out using an L-shaped cannula with a 4 mm tip. A polycarbonate-polyether dialysis membrane (500 µm) with a 20 Kda cutoff was used. The dialysis membrane was inserted in the prefrontal cortex (PFC) while one of the tips of the bipolar stimulation electrode was implanted in the PFC and the other in the VTA. The procedure was performed under ketamine anesthesia.

Microdialysis Protocol

The experiments were carried out in conscious animals, 24 to 72 hours after the surgery. The perfusion medium had the following composition: 147 mM NaCl, 1.2 mM $CaCl_2$, 1.2 mM $MgCl_2$, and 4.0 mM KCl, pH 6.5. In the case of stimulations at high potassium concentrations, sodium ion concentrations were lowered to the same value. In the case of stimulations in the absence of calcium ions, 2.0 mM EGTA was added to the dialysis medium. Dialysates were collected at a rate of 2 µl/min, every 5 minutes, and immediately stored in liquid nitrogen up to analysis.

Analysis of Dopamine and Xanthurenic Acid

These two compounds were quantitatively determined by HPLC chromatography with electrochemical detection. The chromatographic system consisted of a 25 cm×4.6 mm Hypersyl C18 column, maintained at constant temperature. The mobile phase was 0.05 M $NaH_2PO_4$ buffer+0.1 mM EDTA and 6% methanol. Peaks were identified by comparison with the retention times measured on calibration standard solutions.

Electrical Stimulation Protocol

The VTA was stimulated for a period of 10 minutes, with bursts of thirty 0.5-msec pulses for 100 millisec, intensity 100 or 200 µA and at a frequency of 25 Hz.

Determination of In Vitro Yields

These determinations were designed to estimate the quantity of dopamine and XA that crossed the dialysis membrane in the in vivo experiments. Dialysis yields in vitro were approximately 28% and approximately 15% for XA and dopamine, respectively, for a dialysis rate of 1 µl/min at room temperature.

Results

Determination of XA Concentrations in the Extracellular Medium of the PFC

These studies were carried out by determining the different concentrations of XA dialyzed at different dialysis yields. The various dialysis yields were modified by gradually changing the flow rate of the dialysis medium (1, 2, 3 and 4 µl/minute, respectively) and determining the XA concentration in each case. Extrapolation to a rate of zero gives a yield of 100% and an XA concentration in the dialysis medium equal to its concentration in the extracellular medium. The experiment, conducted on 3 different rats, gave a value of XA=6.1 pmol/µl of dialysis medium or cerebral extracellular medium, which gives a mean value of 6.1 µM XA in the extracellular medium of the PFC (FIG. 1).

XA release in PFC After Electrical Stimulation

In two series of experiments, the electrical stimulation was 100 or 200 µA for 10 minutes. After inserting the probe and dialyzing for 1 hour, the baseline value was calculated by dialyzing for a second hour (baseline: 16 to 18 pmol/5 min). A stimulation at 100 or 200 µA gave the same result, indicating that the entire compartment that could be released in our conditions, was released. Compared to a baseline arbitrarily set to 100%, electrically-induced XA release reached 539% while dopamine release reached 655%. Release started immediately after the electrical stimulation, peaked after about 5 minutes of stimulation, then returned to baseline, even if stimulation was continued. A more precise kinetic profile could not be obtained, given the dialysis conditions (5-minute fractions). The results are shown in FIG. 2.

Figure 3:
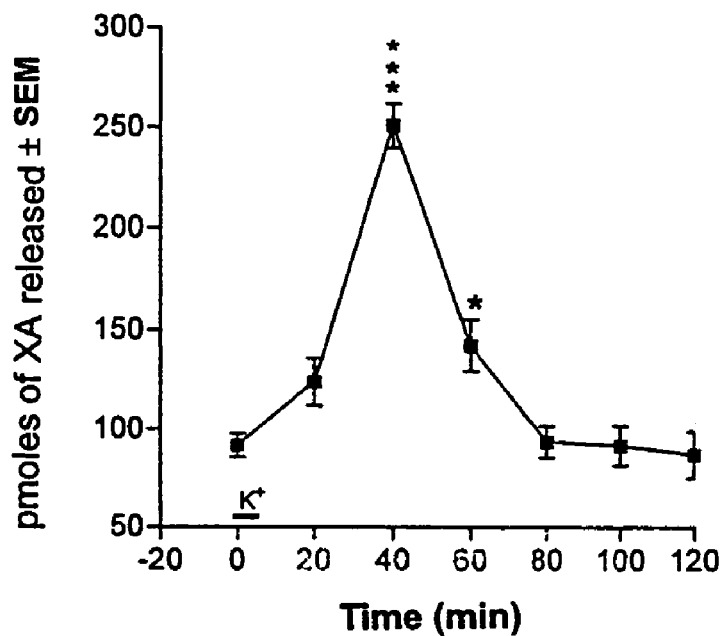

XA release in PFC After Local Depolarization Induced by High Concentrations of Potassium Ions or by 50 µM Veratrine XA release in the PFC extracellular medium was also measured after local depolarization induced by high potassium ion concentrations in the dialysis probe (100 mM KCl for 5 minutes). Before stimulation, baseline release was approximately 92 pmol/20 min. After depolarization, XA release gradually increased to reach 250% of the baseline value after 40 minutes. Levels then gradually returned to baseline which was reached 80 minutes after depolarization (FIG. 3). In the case of veratrine, a 50 µM concentration was placed in the probe for 20 minutes. Baseline XA release (before depolarization) was approximately 96 pmol/20 minutes. After application of veratrine, XA release peaked rapidly, reaching approximately 600% of baseline after 20 minutes, then gradually returned to baseline within about 60 minutes (FIG. 4).

XA Release in PFC Induced by Electrical Stimulation is a Calcium-Dependent Phenomenon In these studies, a group of rats was subjected to electrical stimulation in the VTA and XA release was measured in the frontal cortex. Baseline was 19 pmol/5 min and after electrical stimulation, XA release was 70–75 pmol per 5 minutes of dialysis. The same experiment was repeated, but in this case the dialysis medium did not contain calcium ions, but 2.0 mM EGTA. Under these conditions, baseline XA release was 10 pmol/5 min and electrical stimulation did not induce any increase in XA release (FIG. 5).

XA release in PFC After Electrical Stimulation is Inhibited by Tetrodotoxin, a Sodium-dependent Sodium Channel Blocker This study was conducted on control rats in which XA release was measured in PFC after electrical stimulation. The same experiments were then repeated, but after placing 2.0 µM tetrodotoxin in the dialysis probe for 10 minutes. In these latter conditions, XA release induced by electrical stimulation was completely blocked (FIG. 6).

2. Heterogeneous Distribution of XA in Rat Brain After Peripheral Administration Methods: Rats were given an i.p. injection of XA 50 mg/kg and then sacrificed 30 minutes later by microwave irradiation. Brains were dissected and XA was assayed in 20 different regions of the brain.

Results: The results are presented in the following table (ng/g of brain tissue).

| Brain structure | Physiological concentrations | After injection | Fold increase |
| --- | --- | --- | --- |
| Prefrontal cortex | 146 ± 90 | 1297 ± 351 | 9-fold (**) |
| Frontal cortex | <50 | 1448 ± 165 | 30 (***) |
| Parietal cortex | 416 ± 23 | 2565 ± 692 | 6 (*) |
| Temporal cortex | 110 ± 60 | 995 ± 360 | 9 (*) |
| Caudate-Putamen | 48 ± 4 | 595 ± 294 | 12 (*) |
| Amygdala | 297 ± 13 | 1204 ± 180 | 4 (*) |
| Substantia nigra, VTA | 397 ± 73 | 1307 ± 351 | 3 (*) |

XA accumulated primarily in the frontal and prefrontal cortex (PFC), temporal and parietal cortex, amygdala, dopaminergic nuclei and in the striatum.

Among the different brain structures studied, the following regions did not show significant accumulation of xanthurenic acid: occipital cortex, cingulate cortex, entorhinal cortex, retroslenial cortex, olfactive bulbs, pons, hippocampus, medulla oblongata, cerebellum, thalamus, nucleus accumbens, septum, globus pallidus and hypothalamus.

3. Physiological Concentrations of XA in Different Regions of Rat Brain

Methods: Animals were sacrificed by microwave irradiation and brains were rapidly dissected on a glass slide. Numerous brain structures and nuclei were isolated and stored in liquid nitrogen until analysis. After weighing each structure, the tissues were homogenized in 10 volumes of perchloric acid (mN) and centrifuged. The supernatants were analyzed by HPLC with electrochemical detection. The limit of detection is 0.05 nmoles/g wet weight.

Results: The results are given in FIG. 7. They reveal that concentrations are heterogeneous, being particularly high in the cerebellum and olfactory bulb.

4. Identification and Characterization of Xanthurenic Acid Binding Sites in Rat Brain Protocol for preparation of synaptic membranes:

Synaptic membranes were prepared according to the protocol described below:
1) Whole brains from two male Wistar rats were removed rapidly (decapitation) and weighed.
2) Brains were homogenized in a volume of solution S equal to 10× the weight:
   S=0.32 M sucrose
   10 mM $KH_2PO_4$ pH 6.0
   1 mM EDTA
3°) Homogenizates were centrifuged at 915 g at 4° C. for 10 minutes (Du Pont Instruments, Sorvall RC-5B) and the supernatant recovered.
4°) Centrifugation at 18,200 g at 4° C. for 20 minutes (Du Pont Instruments, Sorvall RC-5B).
5°) The pellet was removed and synaptosomes were ruptured in a volume of distilled water at 0° C. equal to 70× the weight. Polytron for 30 seconds at maximum speed.
6°) Distribution into Beckman centrifugation tubes according to volume and centrifugation at 51,000 g at 4° C. (Beckman, ultracentrifuge L8-70M) for 20 minutes.
7°) The pellets were washed in 50 mM $KH_2PO_4$ buffer pH 6.0 at 0° C.
8°) Distribution into Beckman centrifugation tubes according to volume and centrifugation at 51,000 g at 4° C. (Beckman, ultracentrifuge L8-70M) for 20 minutes.
9°) The pellets were recovered and stored at −80° C.

Part 1: Study of the Pharmacological Characteristics of the Xanthurenic Acid Binding Site Without Ions Binding Protocol Standard Protocol:

Binding was carried out in 50 mM Pipes buffer pH 7.4 at 0° C. (on ice) in the presence of synaptic membranes (from 0.1 to 0.3 mg of protein per tube), tritium-labelled xanthurenic acid ([$^3$H]-XA) at variable concentration according to type of experiment, and either buffer (to determine total binding: TB), or "cold", non-radiolabelled xanthurenic acid (Sigma) at 2 mM concentration (to determine nonspecific binding: NSB). Specific binding (SB) was calculated by subtracting nonspecific binding from total binding. The incubation time was 25 minutes. The filtration by which free [$^3$H]-XA was separated from [$^3$H]-XA bound to its binding site(s) was carried out by rapid aspiration of the incubation medium through Whatman (GF/B) fiberglass filters which were then successively washed twice with cold 50 mM Pipes buffer pH 7.4 (2×3 ml altogether). Filters were placed in scintillation vials to which 5 ml of Rotiszint® (Roth) were added. Vials were counted in a liquid scintillation counter (Beckman LS6000sc).

Protocol for Determining the Effect of pH:

Binding was carried out according to the standard protocol: the incubation medium was prepared from 50 mM Pipes buffer at different pH (pH studied: 5.5; 6.0; 6.5; 7.0; 7.5; 8.0). The concentration of tritiated xanthurenic acid ([$^3$H]-XA) was 200 nM and, for determination of nonspecific binding, non-radiolabelled xanthurenic acid (XA) was used at 2 mM concentration. Nonspecific binding was subtracted from total binding to give specific binding, which varied according to pH. The results shown in FIG. 8 indicate that the optimum pH for xanthurenic acid binding is 7.4–7.5.

Linearity Study Versus Protein Concentration:

Binding was carried out according to the standard protocol: the incubation medium was prepared from 50 mM Pipes buffer pH 7.4 (optimum pH). The amount of protein was varied from 0.04 to 0.5 mg per tube. The tritiated xanthurenic acid ([$^3$H]-XA) concentration was 200 nM and for determination of nonspecific binding, non-radiolabelled xanthurenic acid (XA) was used at 2 mM concentration. Nonspecific binding was subtracted from total binding to give specific binding, which varied according to the amount of protein: the results are linear up to 0.5 mg of protein per tube. The results are given in FIG. 9. Subsequent experiments were carried out using from 0.15 to 0.3 mg of protein per tube.

Measurement of Kinetic Binding Constants:

Association Constant ($k_1$ or $k_{on}$):

Binding was carried out according to the standard protocol: the incubation medium was prepared from 50 mM Pipes buffer pH 7.4 (optimum pH). The tritiated xanthurenic acid ([$^3$H]-XA) concentration was 200 nM and for the study of nonspecific binding, non-radiolabelled xanthurenic acid (XA) was used at 2 mM concentration. The synaptic membrane preparation was added to each tube and rapid filtration was performed at the different time points studied; the incubation times ranged from 1 minute to 40 minutes. Nonspecific binding was subtracted from total binding to give specific binding, which increased over time to reach an equilibrum: equilibrium was attained in about 10–15 minutes. Analysis of the exponential association equation using Graphpad Prism software gave an observed $K_{ob}$ expressed in min$^{-1}$ which is not the same as $k_{on}$. The value of $k_{ob}$ is 0.53±0.16 min$^{-1}$ (FIG. 10).

Equation used for calculation of $k_{on}$:

$$k_{on} = \frac{k_{ob} - k_{off}}{[\text{radioligand}]} \text{ in M}^{-1}\text{min}^{-1}$$

Dissociation Constant or ($k_1$ or $k_{off}$):

Binding was carried out according to the standard protocol: the incubation medium was prepared from 50 mM Pipes buffer pH 7.4 (optimum pH). The synaptic membrane preparation was incubated with tritium-labelled xanthurenic acid (200 nM) for 25 minutes (total binding) after which non-radiolabelled xanthurenic acid (2 mM) was added and incubated for different times to observe dissocation, followed by rapid filtration; incubation times ranged from 1 minute to 45 minutes. Initially, [$^3$H]-XA is bound to its binding site, equilibrium is reached, then the longer the incubation time with non-radiolabelled XA, the greater the decrease in binding, which reflects the dissociation of the [$^3$H]-XA-binding site complex. Dissociation is rapid and analysis of the exponential dissociation equation using Graphpad Prism software gave a dissociation constant $k_{off}$ expressed in min$^{-1}$. The value of $k_{off}$ is 0.33±0.07 min$^-$ (FIG. 11).

These two constants allow an approximate extrapolation of the value for $K_d = k_{off}/k_{on} = 330$ nM.

Saturation Experiment, Actual Measurement of $K_d$ and $B_{max}$:

Binding was carried out in 50 mM Pipes buffer pH 7.4 at 0° C. (on ice) in the presence of synaptic membranes (from 0.1 to 0.3 mg of protein per tube), tritiated xanthurenic acid and either buffer (to determine total binding), or 2 mM non-radiolabelled xanthurenic acid (to determine nonspecific binding). The incubation time was 25 minutes, followed by filtration.

The concentration of tritium-labelled xanthurenic acid was gradually increased so as to reach maximal occupation of the binding sites (saturation plateau). The same thing was done in the presence of an excess of non-radiolabelled xanthurenic acid so as to determine nonspecific binding of [$^3$H]-XA. Then, nonspecific binding was subtracted from total binding to give the specific binding of xanthurenic acid to its binding site(s). Analysis with Graphpad Prism software gave the affinity constant of xanthurenic acid for its binding site(s): Kd=743 nM±250 nM. Similarly, Graphpad Prism allowed determination of the number of binding sites present in a synaptic membrane preparation obtained from whole rat brain: $B_{max}$=6.9±1.2 pmol/mg of protein (FIG. 12).

Competition Experiment, Determination of IC$_{50}$ (50% Inhibitory Concentration):

Binding was carried out in 50 mM Pipes buffer pH 7.4 at 0° C. (on ice) in the presence of synaptic membranes (from 0.1 to 0.3 mg of protein per tube), tritiated xanthurenic acid (200 nM) and either buffer (to determine total binding), or 2 mM non-radiolabelled xanthurenic acid (to determine nonspecific binding), or different concentrations of a non-radiolabelled molecule. If the molecule reversibly binds to the [$^3$H]-XA binding site, the two ligands will compete with each other and a displacement curve of [$^3$H]-can be plotted against the concentration of the competitor molecule. The incubation time was 20–25 minutes after which filtration was carried out.

The radioligand [$^3$H]-XA was prepared by catalytic hydrogenation of 5,7-dichloro-8-hydroxyquinoline-2-carboxylic acid in the presence of palladium/charcoal (10%) in methanol and in the presence of tritium gas.

After purification by HPLC, the compound had an activity of 10 Ci/mmole.

Graphpad Prism software was used to compute the IC$_{50}$ which is the concentration of the compound that produces 50% inhibition of xanthurenic acid binding. In a competition experiment between [$^3$H]-XA and non-radiolabelled XA, a binding displacement curve was obtained which, after analysis by Graphpad Prism software, gave a two site binding model, one IC$_{50}$ at 300 nM and one IC$_{50}$ at 57 μM. This protocol may be used to perform competition experiments with synthetic compounds and thereby to identify or characterize agonists or antagonists, in particular displaying higher affinity for the xanthurenic acid receptor than XA itself.

To this end, before conducting a classical competition experiment to determine an IC$_{50}$, a screening test is first performed, that is to say, the compounds are tested at a relatively low concentration (10 μM) for their ability to displace 200 nM [$^3$H]-XA (using non-radiolabelled XA as control) and one looks to see whether this concentration causes the same or more displacement than this same concentration of non-radiolabelled XA. If so, then an IC$_{50}$ is determined.

The [$^3$H]-XA binding displacement study of tryptophan metabolites (L-kynurenin, 3OH-D,L-kynurenin, 5-hydroxy-L-tryptophan, picolinic acid, 3-hydroxyanthranilic acid) which include xanthurenic acid was also carried out by screening at 200 μM concentration. None of these compounds caused significant displacement of xanthurenic acid. On the other hand, the screening test on kynurenic acid showed no displacement of [$^3$H]-XA from its binding site(s)

but rather a potentiation of this binding. In fact, binding of tritum-labelled xanthurenic acid was higher than what was observed under normal binding conditions.

Effect of Ions on Xanthurenic Acid Binding to its Binding Site(s):

The study of the effect of ions on xanthurenic acid binding to its binding site(s) was carried out in 50 mM Tris maleate buffer pH 6.5 at 0° C. (on ice) in the presence of synaptic membranes (from 0.1 to 0.3 mg of protein per tube), tritiated xanthurenic acid (200 nM) and either buffer (to determine total binding), or 2 mM non-radiolabelled xanthurenic acid (to determine nonspecific binding) and ions at 1 mM concentration. Incubation time was 25 minutes. The following ions were tested: $Cu^{2+}$ ($CuCl_2$); $Zn^{2+}$ ($ZnCl_2$); $Mg^{2+}$ ($MgCl_2$); $Mn^{2+}$ ($MnCl_2$); $Cd^{2+}$ ($CdCl_2$); Sn2+ (SnCl2), $Fe^{3+}$ ($FeCl_3$).

The $EC_{50}$ curves for the different ions (FIG. 14) give preference to copper ions, which have an $EC_{50}$ of approximately 100 μM whereas zinc ions have an $EC_{50}$ of about 500 μM. A copper ion concentration of 100–200 μM roughly corresponds to endogenous concentrations in brain.

Moreover, during our research on endogenous ligands in brain that might play a role at the XA binding site or at a modulating site of this receptor, we observed that adenine and its derivatives [adenosine, adenosine diphosphate (ADP) or adenosine triphosphate (ATP)] showed significant affinity for the xanthurenic acid site and inhibited the binding of tritiated XA. It is highly likely that such derivatives play an important role in modulating the activity of the XA site in brain. Such molecules may represent models for preparing structurally analogous ligands that can interfere with XA sites for the development of therapeutic or pharmacological tools.

Part 2: Study of the Pharmacological Characteristics of the Xanthurenic Acid Binding Site in the Presence Of Copper Ions ($Cu^{2+}$)

Standard Binding Protocol (Protocol Established from the pH, Linearity, Kinetic Constant and Saturation Studies):

Binding was carried out in 50 mM Tris maleate buffer pH 6.5 at room temperature in the presence of synaptic membranes (from 0.1 to 0.25 mg of protein per tube), tritiated xanthurenic acid ([$^3$H]-XA) at variable concentration according to the type of experiment, 200 μM $CuCl_2$ and either buffer (to determine total binding: TB) or "cold", non-radiolabelled xanthurenic acid (Sigma) at 2 mM concentration (to determine nonspecific binding: NSB). Nonspecific binding was subtracted from total binding to give specific binding: SB. The incubation time was 25 min. The filtration by which free [$^3$H]-XA was separated from [$^3$H]-XA bound to its binding site(s) was carried out by rapid aspiration of the incubation medium through Whatman (GF/B) fiberglass filters which were then successively washed twice with 50 mM Tris maleate buffer pH 6.5 at room temperature (2×3 ml altogether). Filters were placed in scintillation vials to which 5 ml of Rotiszint® (Roth) were added. Vials were counted in a liquid scintillation counter (Beckman LS6000sc).

Effect of pH:

Binding was carried out according to the standard protocol: the incubation medium was prepared in 50 mM Tris maleate buffer at room temperature at different pH: 5.5; 6.0; 6.5; 7.0; 7.5; 8.0). The concentration of tritiated xanthurenic acid ([$^3$H]-XA) was 200 nM (+20 μM xanthurenic acid) and, for the study of nonspecific binding, non-radiolabelled xanthurenic acid (XA) was used at 2 mM concentration. The incubation medium contained 200 μM $CuCl_2$. Nonspecific binding was subtracted from total binding to give specific binding, which varied according to pH (FIG. 15): the optimum pH for xanthurenic acid binding is 6.4–6.5.

Linearity Study Versus Protein Concentration:

Binding was carried out according to the standard protocol: the incubation medium was prepared from 50 mM Tris maleate buffer pH 6.5 (optimum pH) at room temperature. The amount of protein was varied from 0.07 to 0.4 mg per tube. The tritiated xanthurenic acid ([$^3$H]-XA) concentration was 200 nM and, for the study of nonspecific binding, 2 mM non-radiolabelled xanthurenic acid (XA) was used. The incubation medium contained 200 μM $CuCl_2$. Nonspecific binding was subtracted from total binding to give specific binding, which varied according to protein concentration: the results are linear up to 0.25 mg of protein per tube (FIG. 16). Subsequent experiments were carried out using between 0.10 and 0.25 mg of protein per tube.

Measurement of the Copper Dose/Effect on Xanthurenic Acid Binding:

Binding was carried out according to the standard protocol: the incubation medium was prepared from 50 mM Tris maleate buffer pH 6.5 (optimum pH) at room temperature. The copper ($CuCl^2$) concentration was varied from $3.10^{-7}$ M to $3.10^{-4}$ M. The tritiated xanthurenic acid ([$^3$H]-XA) concentration was 400 nM (+20 μM xanthurenic acid) and, for the study of nonspecific binding, 2 mM non-radiolabelled xanthurenic acid (XA) was used. Analysis of the dose-effect curve by Graphpad Prism software gave an $EC_{50}$ (50% effective concentration) of 33.4 μM with a Hill coefficient=1.8 (FIG. 17).

Saturation Experiment, Actual Measurement of $K_d$ and $B_{max}$

Binding was carried out in 50 mM Tris maleate buffer pH 6.5 at room temperature in the presence of synaptic membranes (from 0.10 to 0.25 mg of protein per tube), tritiated xanthurenic acid and either buffer (to determine total binding), or 2 mM non-radiolabelled xanthurenic acid (to determine nonspecific binding). The incubation time was 25 minutes, followed by filtration.

The concentration of tritium-labelled xanthurenic acid was gradually increased so as to reach maximal occupation of the binding sites (saturation plateau). The same thing was done in the presence of an excess of non-radiolabelled xanthurenic acid so as to determine nonspecific binding of [$^3$H]-XA. Then, nonspecific binding was subtracted from total binding to give the specific binding of xanthurenic acid to its binding site(s). Analysis with Graphpad Prism software gave the affinity constant of xanthurenic acid for its binding site(s): $K_d$=7.56 μM±0.8 μM. Similarly, Graphpad Prism allowed determination of the number of binding sites present in a synaptic membrane preparation obtained from whole rat brain: $B_{max}$=581.8±33 pmol/mg of protein (FIG. 18).

Competition Experiment, Determination of $IC_{50}$ (50% Inhibitory Concentration):

Binding was carried out in 50 mM Tris maleate buffer pH 6.5 at room temperature in the presence of synaptic membranes (from 0.1 to 0.3 mg of protein per tube), tritiated xanthurenic acid (200 nM) and either buffer (to determine total binding), or variable concentrations of non-radiolabelled xanthurenic acid ($10^{-3}$ M to $10^{-10}$ M). Graphpad Prism software was used to compute the $IC_{50}$ which is the concentration of the compound that produces 50% inhibition of xanthurenic acid binding. In a competition experiment between [3H]-XA and non-radiolabelled XA, a binding displacement curve was obtained which, after analysis by Graphpad Prism software, gave a two site binding model, one $IC_{50}$=1 μM and one $IC_{50}$=114 μM (FIG. 19).

Study of the Regional Distribution of XA Binding Sites in Rat Brain by Quantitative Autoradiography Followed by Image Analysis Method: Brains from three adult male Wistar rats were rapidly dissected after decapitation and frozen in isopentane kept at −40° C. on dry ice. The brains were then cut with a cryostat into slices 20 µm thick. The slices were spread on glass slides which were then rapidly dried in cold air. The slides, mounted in a frame, were then incubated for 10 minutes in 50 mM Pipes buffer pH 7.4 kept at 0° C. on ice. The slides were then immersed for 20 minutes in the same buffer supplemented with 200 nM radiolabelled XA. After three brief 10-second washes with Pipes buffer without the radiolabelled ligand, the slices were dried in a stream of cold air. They were then exposed to tritium-sensitive film in the dark. After two months' exposure in airtight cassettes, the films were developed and shades of gray were digitized and compared with an arbitrary tritium radioactivity scale, calibrated in Curies per gram equivalent tissue (Amersham). The results, which represent the distribution of XA receptor density in various regions of rat brain, within a factor of one, are given in the following table.

Regional distribution of [$^3$H] xanthurenic acid binding sites.
(Serial 20 µm slices of brain, Wistar rats).

| Brain structure | | Integrated densitometric value nCi/g ± SD (n = 3) | |
| --- | --- | --- | --- |
| Lateral caudate nucleus | 195 ± 3.1 | 1942.6 ± 30.3 | 252.0 ± 4.0 fmol/mg |
| Compact substantia nigra (A$_9$) | 126 ± 2.0 | 806.5 ± 13.8 | 104.6 ± 1.8 |
| Interpeduncular nucleus | 127 ± 4.3 | 822.9 ± 17.3 | 106.8 ± 2.2 |
| Central amygdala nucleus | 194 ± 4.3 | 1921.3 ± 42.9 | 249.4 ± 5.6 |
| Dorsal hippocampus | 203 ± 9.8 | 2068 ± 41.1 | 268.5 ± 5.3 |
| Ventral hippocampus | 128 ± 2.1 | 847.5 ± 16.9 | 110.0 ± 2.2 |
| Mediodorsal thalamic nucleus | 172 ± 3.5 | 1568.8 ± 39.3 | 203.7 ± 5.1 |
| Median post. thalamic nucleus | 180 ± 7.5 | 1701 ± 69.9 | 220.9 ± 9.0 |
| Dorsomedian hypothalamus | 180 ± 6.3 | 1700 ± 73.2 | 220.7 ± 9.5 |
| Ventral tegmental area (A$_{10}$) | 119 ± 7.5 | 691.8 ± 43.6 | 89.8 ± 5.6 |
| Lateral nucleus accumnbens | 193 ± 10 | 1904.9 ± 99.0 | 247.3 ± 12.8 |
| Dorsal raphe nucleus (B$_7$) | 121 ± 10 | 724.5 ± 59.8 | 94.1 ± 7.7 |
| Median raphe nucleus (B$_8$) | 110 ± 2.0 | 544.2 ± 16.9 | 70.6 ± 2.2 |
| Cerebellar lobes | 180 ± 3.5 | 1740.9 ± 58.5 | 226.0 ± 7.6 |
| Parietal cortex | 184 ± 1.4 | 1757.3 ± 23.3 | 228.2 ± 3.0 |
| Temporal cortex | 115 ± 7.7 | 634.4 ± 52.3 | 82.4 ± 6.8 |
| Ant. cingulate cortex | 180 ± 5.2 | 1691.8 ± 49.5 | 219.7 ± 6.4 |
| Prefrontal cortex | 180 ± 11.5 | 1691.8 ± 108.2 | 219.7 ± 14.0 |
| Periaqueductal gray substance | 125 ± 5.65 | 724.5 ± 40.0 | 94.1 ± 5.2 |
| Pyriform cortex | 186 ± 7.7 | 1798.3 ± 91.7 | 233.5 ± 11.9 |
| Olfactive bulbs | 181 ± 7.0 | 1703 ± 81.5 | 221.2 ± 10.6 |
| Medulla oblongata | 149 ± 4.9 | 1249.1 ± 50.7 | 162.2 ± 6.6 |
| Globus pallidus | 163 ± 7.7 | 1413.2 ± 67.2 | 183.5 ± 8.7 |
| Lateral septum nucleus | 175 ± 6.1 | 1609 ± 55.7 | 208.9 ± 7.2 |
| Median septum nucleus | 147 ± 14.9 | 1150 ± 116.3 | 149.4 ± 15.1 |
| Occipital cortex | 152 ± 51 | 1232 ± 291.7 | 160.0 ± 37.8 |

5. Study of XA Modulation of Dopaminergic Activity in the Striatonigral and Meso-Cortico-Limbic Tracts Materials and Methods Animals: Adult male Wistar rats weighing 250 to 275 g were housed in pairs in plastic cages with a standard 7 a.m.–7 p.m. light cycle and free access to food and water. Animals studies were conducted in accordance with the requirements of the EEC directive of 24 Nov. 1986 (86/609/EEC).

Chemicals: XA, 6-OHDA hydrobromide, 2,4,5-trihydroxyphenylethylamine and desipramine were purchased from Sigma. NCS-486 was produced by the Laboratoire de Pharmacochimie of the CNRS in Strasbourg.

Surgical protocol: An L-shaped cannula with 4 mm tip (CMA 12, Carnegie, Sweden) was used for the experiments. The dialysis membrane, 500 µm in diameter, was made of polycarbonate-polyether with a 20 Kda cutoff. The probe guide was implanted in the PFC under stereotactic guidance. Animals were anesthetized with ketamine hydrochloride (150 mg/kg i.p.)

Lesions Induced by 6-hydroxydopamine in Dopaminergic Nuclei A9 and A10

Animals were anesthetized with ketamine (100 mg/kg i.p.). 6-OHDA was dissolved at a concentration of 4 µg/µl in physiological serum containing 0.01% ascorbic acid. One microliter was injected over 2 minutes into A9/A10 using a Hamilton syringe under stereotactic guidance. After the injections, the toxin was allowed to diffuse for 1 minute. Noradrenergic neurons were protected by prior injection of desipramine 25 mg/kg i.p., 45 minutes before injection of 6-OHDA.

Four weeks later, rats received apomorphine 1 mg/kg by subcutaneous injection and the number of controlateral rotations executed 15 minutes after the injection was recorded.

The rats with induced lesions performed 130±45 turns/15 minutes. Six weeks after local injection of 6-OHDA in the right A9/A10 dopaminergic nuclei, rats displaying good functional alteration were selected and implanted for the microdialysis studies.

Microdialysis Protocol

The experiments were carried out in conscious rats with and without induced lesions, 24 to 48 hours after surgical insertion of the microdialysis probe. The composition of the microdialysis medium was as follows: 147 mM NaCl; 1.2 mM CaCl$_2$; 1.2 mM MgCl$_2$; 4.0 mM KCl, pH 6.5. The dialysis rate was 1 µl/min (CMA 100 pump, Carnegie). Dialysates were collected in 20 minute fractions and stored immediately in liquid nitrogen pending analysis.

Analysis of Dopamine, DOPAC and HVA in the Microdialysis Medium

These compounds were analyzed by HPLC with electrochemical detection. The chromatographic system consisted of a 25 cm×4.6 mm C18 column maintained at a constant temperature of 30° C. The mobile phase was 50 mM NaH$_2$PO$_4$ containing 0.1 mM EDTA and 6% methanol, the pH of the solution was adjusted to 4.85.

In Vitro Yields

The in vitro dialysis yield for dopamine was previously determined to be 16% at laboratory temperature and for a dialysis rate of 1 µl/minute.

Histology

After the experiments, the correct positioning of the probe was always checked by post-mortem histological examination of the brain after fixation in paraformaldehyde.

Statistical Analyses

The microdialysis experiments were statistically analyzed by an ANOVA followed by a Newman-Keuls test of multiple comparisons.

Results

Dose/effect of Local XA Infusion in the PFC on Extracellular Dopamine Concentrations Retrodialyzed XA concentrations were respectively 1 µM (black circles), 5 µM (black squares) and 20 µM (black triangles). XA was applied during a 20 minute dialysis. The results are expressed as the percentage of mean baseline dopamine release (determined on eight 20-min dialysis fractions prior to stimulation by XA) (FIG. 20).

The lowest XA concentration (1 µM) had no effect on dopamine release. On the other hand, the 5 µM concentration (approximately 1.5 µM XA in brain tissue based on in vitro yields) increased extracellular dopamine release by approximately 250%. The 20 µM concentration (about 6 µM in tissue) increased dopamine release by 400–450%.

Effects of Local Application of 20 µM XA in the PFC on Release of Dopamine, DOPAC and HVA The results are expressed as the percentage of dopamine release relative to baseline (determined on eight 20-min dialysis fractions prior to injection of XA), FIG. 21. Black squares represent dopamine, black circles represent DOPAC and white squares represent HVA. In this case, as seen previously, dopamine release was increased by 400–450% from baseline after 20 minutes, but DOPAC and HVA release decreased slightly after 100 to 120 minutes.

Effects of Local Application of 20 µM XA in the PFC on Extracellular Dopamine Release, in the Presence or Absence of 20 µM NCS-486

The results are expressed as the percentage of dopamine release relative to baseline (mean of eight 20-min dialysis fractions prior to injection of XA) (FIG. 22: application of 20 µM XA for 20 minutes (black circles), or co-infusion of 20 µM XA+20 µM NCS 486 (white squares) or application of 20 µM NCS-486 alone (white triangles)). It can be seen that treatment with NCS-486 alone or with NCS-486+XA did not modify dopamine release, while XA alone increased dopamine release by approximately 300%, about 40 minutes after the stimulation.

6. Electrophysiological Studies

Electrophysiological Recordings

The neuron cell line NCB-20 was studied by using the patch-clamp technique (Hamill et al., 1981) in the so-called cell-attached patch configuration. The recording media were designed so that only the activity of single aspecific cation channels and chloride channels located in the membrane fragment under the pipette would be recorded. Specific calcium, sodium and potassium currents were minimized by replacing the majority of cations in the pipette medium by an impermeant cation, N-methyl-D-glucamine (NMDG) or blockage by TEA (tetra-ethyl-ammonium). Replacement of permeant cations in the pipette by NMDG also made it possible to have aspecific cation currents mainly in the outflux direction since the influx component was minimized. Furthermore, in some experiments, chloride channel activity was recorded only in the influx direction by replacing chloride ions in the pipette medium by TCA (trichloroacetic acid). Control of cell membrane potential at a value close to zero mV was achieved by using an extracellular KCl medium. Thus the potential of the recorded membrane fragment corresponds to the opposite of the potential imposed in the recording pipette. Under these conditions the recording media had the following composition (in mM): NMDG/Cl (or TCA) 140, KCl 2, $MgCl_2$ 1, HEPES 10, TEA/Cl 15, for the pipette medium and NaCl, KCl 141, $CaCl_2$ 0.5, HEPES 10, EGTA 5, for the bath; in both cases the pH was adjusted to 7.4 with TRIS base and KOH, respectively.

Chemicals were from Sigma (Saint Quentin Fallavier, France).

After making a gigaseal with pipettes having a resistance comprised between 4 and 7 MΩ, ion currents were measured with a patch-clamp amplifier (EPC-7 amplifier, List-Medical, Darmstadt, Germany or Axopatch B200, Axon Instruments, CA). Signal acquisition (acquisition frequency from 1 to 5 kHz) was then done using an interface card (Scientific Instruments, OH) and pClamp 6 software (Axon Instruments, CA). The products were diluted to the desired concentration in the extracellular medium. Application was by gravity through a multipore perfusion system with an internal pore diameter of 300 µm. The solution was changed by placing the corresponding pore opposite the recorded cell after opening the valve.

Results

NCB-20 cells express a binding site specifically recognized by xanthurenic acid. These functional experiments aimed to detect any electrogenic membrane phenomenon that might be activated by xanthurenic acid receptor(s). There is some evidence suggesting that this receptor is coupled to G proteins and that a membrane effect would therefore occur through an intracellular relay. Accordingly, we investigated an eventual action on cation and chloride channels, whose activation depends on both membrane potential and cystolic factors (mainly the calcium ion and kinase proteins; Evans and Marty, 1987; Taleb et al., 1988; Leech et al., 1996). These two types of ion channel were therefore recorded singly (see methods) and by imposing one or the other of the two permeabilities. The inversion potential of the response would be comprised between −49.5 or −11.8 mV, respectively, for a cationic (monovalent cations) or chloride response. Under these conditions any change in cytoplasmic factors will also be revealed by the parameters characterizing the current-potential relationship (FIG. 23).

Cells were recorded in the cell-attached patch configuration. The current crossing the channels inserted in the membrane under the pipette was recorded singly. The cell membrane potential was set at 0 mV by a KCl concentration in the extracellular medium equivalent to that of the cytoplasm. Under these conditions the potential of the membrane fragment under the pipette is opposite to that of the pipette.

Effect of Xanthurenic Acid on Activation of the Cation Current

The membrane fragment under study was periodically stimulated (frequency 0.2 Hz) by a potential gradient of −70 to 100 mV (see protocol in FIG. 24A, lower trace). In control conditions using a pipette medium depleted of chloride ion (replaced by TCA), the recorded current was stable and had an amplitude of −0.4±0.1 and 8.6±0.2 µA (n=30) at potentials of −70 and 100 mV, respectively. This current reversed at a potential of 48.3±3.5 mV (n=3). This value, which is close to the inversion potential of monovalent cations (−49.5 mV, if intracellular concentrations of $K^+$ and $Na^+$ are estimated at 140 and 2 mM, respectively), shows that under these recording conditions, there is a selective basal permeability to cations. The current-potential relation shows a marked outflux rectification (FIGS. 24A and C), in agreement with the asymmetrical distribution of cations on either side of the membrane fragment recorded. In the presence of xanthurenic acid at concentrations of 1 to 20 µM after a latency (from 1 to 4 minutes) dependent on the agonist concentration, the amplitude of the cation current increased by 10 to 40% with a slow kinetics to which can be added transient large amplitude currents. In the case of FIG. 24, the current amplitude at the peak of the transient current and at 100 mV potential was increased by a factor of 5.

On average, for an agonist concentration of 20 μM, the current amplitude increased by a factor of 5.0±1.7 (n=3). The I-V relationship of the current specifically activated in the presence of xanthurenic acid (after subtracting the current observed in control conditions) was similar to that of the control current (FIG. 24C). In particular, the inversion potential was virtually identical to that of the control and had a mean value of −51.6±2.1 (n=3). This is true for both the slow current and the transient current. This inversion potential is close to the equilibrium potential of monovalent cations suggesting that in these conditions, xanthurenic acid can induce the activation of a current of the cationic type. The observation that such current is recorded on a membrane fragment physically isolated from the rest of the cell where the agonist is applied, indicates that activation of such cation channels occurs through an intermediary intracellular relay between the receptor and the ion channel.

To answer the question of whether such cation channels also allow passage of divalent cations, calcium in particular, we performed the same type of experiment as hereinabove but with a pipette medium containing mainly the $Ba^{2+}$ ion (all monovalent cations were replaced by $Ba^{2+}$ except 2 mM $K^+$ ions and 15 mM $TEA^+$ ions). Under these conditions as well, in the presence of xanthurenic acid we observed the activation of the current whose inversion potential in this case had a mean value of 2.6±2.5 mV (n=7). Replacing monovalent cations by $Ba^{2+}$ shifted the inversion potential of the response by approximately 54 mV. In the case where $Ba^{2+}$ ions would not participate in the current activated by the agonist, the predicted inversion potential would have a value of −53.5 mV. The observed difference reflects the passage of $Ba^{2+}$ ions through the cation channels.

Effect of Xanthurenic Acid on Activation of a Chloride Current

On some responses, however, particularly those not showing a transient current, we observed a variation in the inversion potential of the current induced by the agonist. For instance, in the case illustrated in FIG. 25, the onset of the response had an inversion potential of −16.5 mV which reflects contamination of the cation current by another current whose equilibrium potential has a more depolarized value. In a second phase of the response the potential has shifted towards an even more depolarized value of −4.2 mV. The added current has an inversion potential compatible with a movement of chloride ions in our experimental conditions.

Pharmacology of the Response to Xanthurenic Acid

NCS-482 applied at a concentration of 10 to 20 μM to NCB-20 cells induced a response virtually identical to that of xanthurenic acid (FIGS. 25 and 26). This result indicates that NCS-482, a xanthurenic acid derivative able to displace xanthurenic acid binding, acts as an agonist of the xanthurenate receptor. NCS-486, another xanthurenic acid derivative which also displaces xanthurenic acid binding, had no effect when applied alone (20 μM), whereas it reduced the amplitude of the agonist-induced response (FIG. 26), which makes it a xanthurenate receptor antagonist.

7. Neuropharmacology of Xanthurenic Acid (XA): Behavioral Studies in the Rat

1) Infrared Cell Measurements of Locomotor Activity

The following doses were studied: 12.5, 25, 37.5, 50, 100 and 200 mg/kg (i.p.) (FIG. 27). This test demonstrated a decrease in motor activity, and this at XA doses greater than or equal to 50 mg/kg.

The intensity of sedation was proportional to the injected dose.

2) Measurement of Global Reactivity of the Animals by the "Open Field" Test

This test confirmed the absence of sedation at a dose of 37.5 mg/kg, the dose at which exploration of the center of the cage was significantly increased, which might be interpreted as a potential anxiolytic effect (FIG. 28). This tendency was confirmed by a test evaluating social interactions between two congeners (Ramos et al., Behav. Brain Res., 1997, 85: 57–69). The 50 mg/kg dose produced a significant increase in the duration of social interactions in treated animals as compared to untreated control congeners. At the 100 mg/kg dose, this evaluation was hindered by a significant sedative effect induced by the product.

3) Demonstration of an Effect of the Antidepressant Type by the Porsolt Test

The following doses were used: 50, 100, 150 and 200 mg/kg i.p.

This test has been validated with imipramine 30 mg/kg. The test described by Porsolt et al., Eur. J. Pharmacol. 1978, 47: 379–391, was used.

Doses of 100, 150, 200 mg/kg produced a statistically significant decrease in the cumulative duration of immobility, indicating that the effect obtained was similar to that of imipramine (FIGS. 29 and 30).

4) Demonstration of an Effect of Xanthurenic Acid on Memorization Processes by the Object Recognition Test Ennaceur and Delacour, Behav. Brain Res. 1988, 31: 47–59.

Doses of 37.5 and 75 mg/kg i.p. were used.

The results (FIG. 31) revealed a significant increase in the object recognition score for treated animals as compared to controls. The increase in the score can be interpreted as a beneficial effect of the product on short-term memory.

5) Effects of Xanthurenic Acid After Intracerebral Injections

The product was injected by the intracerebroventricular route (i.c.v.) on the one hand, and in defined brain structures on the other hand: ventral tegmental area (A10), substantia nigra (A9) or nucleus accumbens. At XA doses of 2, 4, 10, 50 μg/rat, dose-related stereotypies were observed. After disappearance of the stereotypies (30±15 minutes), reinjection of XA induced the same effects.

6) Study of the Antagonist Potential of NCS-486 on Animals With Unilateral Lesions of the Striatonigral and Mesocorticolimbic Tracts Induced by Intracerebral Injection (VTA; SNc) of a Neurotoxin (6-OHDA) After Protection of Noradrenergic Neurons by Pretreatment With Desipramine Injection of a non-sedative dose of XA (25 mg/kg i.p.) did not antagonize the controlateral rotations induced by apomorphine (0.05, 0.1 mg/kg s.c.) Studies of the potentiation of ipsilateral rotations induced by amphetamine and possible antagonism by NCS486 of ipsilateral rotations induced by xanthurenic acid 25 mg/kg i.p. are under way.

7) Electroencephalographic (EEG) Analysis of Sedation Induced by i.p. Injection of Xanthurenic Acid Doses tested ranged from 50 to 500 mg/kg i.p. The detailed EEG analysis did not show evidence of "epileptogenic" or "deep NREM sleep" activity. Only a reduction in the amplitude of the EEG waves was observed. This sedation was accompanied by a significant, dose-related decrease in body temperature (−0.5 to −2° C.).

IN CONCLUSION, the neuropharmacological studies conducted in rats treated with xanthurenic acid either by peripheral or local administration, showed the following:

XA has sedative activity in animals, with a very clearcut dose-effect relationship. Such sedative effect is corroborated by several tests. In the open field test which evaluates the spontaneous behavior of the animals, XA was found to exert an anxiolytic effect at non-sedative doses and it promoted social interactions. Certain tests aiming to evaluate an antidepressant effect of XA revealed a dose-dependent mood enhancement in animals. Memory tests showed that XA promotes short-term memory. Finally, this substance has potent dopaminergic activity as demonstrated by the induction of stereotypies. Such stereotypies are blocked by high doses of the antagonist NCS-486. EEG studies showed that XA has no epileptogenic effects and does not induce deep NREM sleep, although a decrease in the amplitude of the EEG waves and hypothermia were observed, two phenomena which may be correlated with sedation.

8. Demonstration and Characterization of an XA Transport System in Cultured Neurons 1) Materials and Methods NCB-20 cell cultures Maintenance of the cell line:

NCB-20 cells were stored frozen in liquid nitrogen as aliquots of the parent strain. For the purposes of an experiment, an aliquot was thawed and placed in culture conditions appropriate for the study. To maintain the cell line, as soon as the culture dish reached confluence, the initial dish was used to inoculate another dish by taking only an aliquot of the cell suspension in the original dish. In this manner, subcultures were carried out in DMEM medium supplemented with 10% fetal calf serum (FCS) and dilution was generally by a factor of ten.

Culture of Differentiated NCB-20 Cells:

The cell culture was prepared by using a culture dish of NCB-20 cells at 80% confluence. The culture medium was removed and replaced with 10 ml of DMEM supplemented with 10% FCS. Cells were then detached and suspended by repeated passage of the medium through a 2 mm gauge needle. Cells were then counted in a hemocytometer. The final suspension was adjusted to a cell density of $3.10^4$ cells/ml in DMEM medium supplemented with 10% FCS and 1 mM cAMP. Petri dishes were seeded with 2 ml of this suspension and incubated at 37° C. in a moisture-saturated $CO_2$ atmosphere. Cells were used four days after inoculation.

Measurement of XA Transport in NCB-20 Cells

The culture medium of 4-day NCB-20 cell cultures differentiated in cAMP was replaced by one of the buffer solutions described hereinabove (Krebs with or without $Na^+$, to respectively evaluate $Na^+$-dependent active transport and passive transport, which occurs mainly through diffusion) according to the type of experiment planned. Culture dishes were placed in a water bath at 37° C. for 10 minutes. The buffer was then replaced by the same buffer solution containing [$^3$H]-XA and XA at concentrations ranging from 1 to 500 μM. [$^3$H]-XA was present at very low concentration and served only as a tracer of the cold (non-radiolabelled) XA. After 1 minute of incubation, the solutions were aspirated and the cells washed three times for 10 seconds with 1 ml of the same buffer (Krebs with or without $Na^+$), kept on ice. Active transport requires energy (ATP) and is markedly slowed at temperatures below 37° C. The washed cell layer was frozen in dishes then, the next day, distilled water was added to obtain a solution of cellular debris containing the intracellular radiolabel ([$^3$H]-XA). Freezing facilitated homogenization by repeated passage of the solution through a pipette. A 900 μl aliquot was added to scintillation fluid (Rotiszint®, 4 ml). The remainder of the solution was sampled to assay protein by the BCA method (Uptima). The radioactivity measured in the scintillation counter was converted by means of a suitable calibration curve into picomoles of XA taken up by the cells per mg of protein.

The same procedure was carried out for each dish containing the differentiated cells. However, in each experiment, one of the parameters was modified so as to determine the kinetic and pharmacological characteristics of XA transport in NCB-20 cells.

The conditions of transport were measured as a function of:

Incubation Time:

These experiments defined the kinetics of XA transport. For each incubation time, transport was measured on nine dishes of NCB-20 cells with $Na^+$ and without $Na^+$. Ten different time points were studied: 0-10-30 seconds and 1, 2, 3, 5, 8, 10, 12 minutes. Four different experiments were carried out.

[$^3$H]-XA Concentration:

These studies defined the kinetic constants: maximal velocity of transport ($V_m$) and XA concentration required to attain half-maximal velocity ($K_m$).

For each XA concentration, XA transport was measured on nine dishes of NCB-20 cells with $Na^+$ and nine dishes without $Na^+$. Seven different concentrations were tested: 1-5-12.5-25-50-100-200 μM. Four independent experiments were carried out.

Protein Assay

Protein was assayed by the microplate technique. The microplate must have the required number of wells to perform a duplicate assay for each culture dish and for a standard curve.

The cells at the bottom of each treated culture dish were taken up in 1 ml of doubly-distilled water. Several aspirations-releases were performed to detach all the cellular debris and homogenize the suspension. Two 20 μl test samples were then removed and placed in the wells of the microplate.

A space was reserved for the calibration curve ranging from 0.032 to 2 mg/ml. Each suspension of cellular debris was measured in duplicate. Two hundred microliters of reagent (mixture of 50 parts reagent A and one part reagent B) were then added to each well. The plate was shaken and incubated at 37° C. for 30 minutes.

Radioactivity Counting

Four milliliters of scintillator were added to the tubes containing 900 μl of the cell suspension obtained. The control tube contained 900 μl of doubly-distilled water, and the tubes used to measure specific activity contained 10 μl of the radioactive solutions used as reagent during the experiment and 890 μl of doubly-distilled water. The tubes were closed, vortexed and left overnight at 4° C. before being counted in the scintillation counter. This count measures intracellular radioactivity which is directly proportional to the quantity of XA that entered the cell through passive or active transport. To calculate the amount of active transport, passive transport (Krebs without Na$^+$) is simply subtracted from total transport (Krebs with Na$^+$).

2) Results Concerning XA Transport

All calculations were performed on the Excel computer program. The results were then converted to graphic form with Prism 3.0 software which also computed the equations of the line and statistical analysis.

The results concerning XA transport in NCB-20 cells over time are given in FIG. 32.

In the study of transport as a function of incubation time of the cells in the presence of XA, three similar-looking curves were obtained. Transport increased by about 20% in the presence of sodium. The three curves reached a plateau after approximately 1 minute, thus defining the optimal time at which to measure XA transport in NCB-20 cells. This 1-minute time was used in subsequent experiments.

The results concerning XA transport in NCB-20 cells according to [$^3$H]-XA concentration are given in FIG. 33.

The Scatchard plot gives the mathematical constants of intracellular transport of XA, with $K_m=105$ μM and $V_{max}=1229$ pmoles/mg protein/minute.

In the study of XA transport as a function of XA concentration, saturation of transport and therefore of the transporter was observed, which can be mathematically defined by the value of the maximal velocity of transport, which in our experiments is $V_{max}=1229\pm440$ pmoles/mg protein.min. Another mathematical constant which characterizes transport is the $K_m$, which is the concentration of XA needed to attain half the maximal velocity. In our experiments, $K_m=105\pm81$ μM.

The optimal XA concentration for the pharmacological studies on this molecule will be 100 μM, which corresponds to the calculated $K_m$.

Interference of Other Endogenous Molecules with XA Transport

Other endogenous molecules which might be transported by the XA transporter were tested. In addition, to demonstrate the energy-dependent nature of this transport, we blocked cellular energy production with deoxyglucose which inhibits glycolysis. The results are shown in the histogram in FIG. 34 as the percentage entering the cells relative to transport in the presence of radiolabelled XA alone (=100%).

L-tryptophan, L-tyrosine and kynurenic acid were found to be good inhibitors of cellular transport of XA. It may therefore be possible that uptake of XA by neurons makes use of the transporter of neutral amino acids. The presence of copper ions or zinc ions in the medium led to a highly significant potentiation of XA transport (3-fold higher for copper ions). The presence of the cellular poison 2-deoxyglucose caused an approximate 50% decrease in transport, indicating that transport requires intact cellular energy production.

3) Conclusions of XA Transport Studies

The different experiments carried out reveal the presence of an active transport system for XA in NCB-20 cells. Such transport is an active phenomenon which requires the presence of sodium ions in the reaction medium. The transport is characterized by fairly rapid kinetics since the optimal velocity is reached after an incubation time of about 1 minute. The kinetic constants of this active transport system were measured and the maximal velocity was found to be 1229 pmoles/mg protein.min with $K_m=105$ μM. Some amino acids, including tryptophan and tyrosine, inhibit this transport, suggesting that the transporter involved may be a neuronal transporter for neutral amino acids and that XA transport interferes with the transport of amino acids essential for catecholamine and serotonin synthesis. The synthetic compounds, which are XA receptor ligands, could be tested on this transporter to check their specificities.

9. Organization and Role of the XA System in the Regulation of Dopaminergic Activity 1) Is XA Co-Released With Dopamine at the Same Nerve Terminals Upon Stimulation of Dopaminergic Nuclei $A_9$–$A_{10}$?

To investigate this question, we studied the modifications of extracellular XA and dopamine release that occur after inducing lesions in dopaminergic nuclei with 6-hydroxydopamine (6-OHDA). This lesion destroys in particular the dopaminergic nerve terminals in the frontal cortex. We further investigated the effects of XA on glutamate and GABA release in an attempt to elucidate the sequence of events leading to the modification of dopamine release in the frontal cortex in rats.

Protocol:

A unilateral lesion in the mesencephalic dopaminergic tract was induced by stereotactic injection of 6-hydroxydopamine hydrobromide (6-OHDA HBr, Sigma) into the ventral tegmental area (VTA) and the compact substantia nigra (SNc). The procedure was performed under stereotactic guidance (Narishige) on Wistar rats under imalgene anesthesia (100 mg/kg i.p.). The neurotoxin 6-OHDA was dissolved in isotonic sodium chloride solution (0.9% NaCl) containing 0.01% ascorbic acid at a final concentration of 4 μg free base per μl and 6 μg (1.5 μl per injection) were injected over 2 minutes through a 20G stainless steel injection cannula. In agreement with the Paxinos and Watson atlas, the stereotactic coordinates used are expressed in millimeters relative to the bregma: AP: 2.3; ML: 0.5; DV: 8.7 mm and AP: 2.3; ML: 2.0; DV: 7.5 mm, respectively for the VTA and SNc. The dorsoventral coordinate was taken from the cranial bone, the ear bars being positioned 3.3 mm below the bar of the upper incisors. After injecting the entire volume at a rate of 1 μl/min (CMA 100 pump), the needle was left in place for 1 minute more so as to allow the toxin to diffuse freely around the injection site. Noradrenergic neurons were protected from damage by prior injection of desipramine 25 mg/kg i.p. 45 minutes before injection of 6-OHDA.

Selection of Animals

Four weeks after induction of the lesions, the rats were tested after subcutaneous administration of a direct agonist (apomorphine 0.1 and 1.0 mg/kg) and the number of controlateral rotations (side opposite to the lesion) in 15 minutes was recorded. The result for rats treated with the neurotoxin was as follows: 130±45 turns/15 minutes (n=12 animals).

Six weeks after the injections in the right compact substantia nigra and ventral tegmental area, rats with a satisfactory result in the apomorphine-induced controlateral rotation test were selected and implanted for the microdialysis experiments.

On completion of the experiments the animals were sacrificed. The striatum and ipsilateral and controlateral mesencephalic nuclei were removed and analyzed by HPLC for residual dopamine content.

The results, expressed in pmoles/g of wet tissue±SEM (n=3) are as follows:

Damaged striatum: 261±123 versus intact striatum 9140±1413 (−98% p=0.0033)

Damaged VTA —SNc: 32±31 versus intact VTA —SNc 563±128 (−95% p=0.0157).

These results indicate that the lesion of dopaminergic neurons was satisfactory and that there was a very marked decrease in dopamine levels in the striatum and dopaminergic nuclei.

Measurement of Extracellular Release of Dopamine and its Metabolites After Neurotoxin-induced Lesion of Mesencephalic Dopaminergic Nuclei:

Neurotoxin-treated animals were implanted with the dialysis probe and bipolar electrode, electrically stimulated in the VTA (100 and 200 µA) and dialyzed in the prefrontal/anterior cingulate cortex according to the same protocol described for the previous experiments.

Among the measured parameters (DA, DOPAC, HVA, XA and 5-HIAA), only XA and 5-HIAA were detectable on the chromatograms.

The results show that electrical stimulation (100 and 200 µA) of the VTA after 6-OHDA-induced lesion of dopaminergic nuclei (VTA and SNc) induced XA release in the frontal cortex (+151±51% and +667±115% for stimulation with 100 µamperes and 200 µamperes, respectively), accompanied by release of 5-HIAA without modifying residual dopamine release (DA, DOPAC and HVA) after lesion induction.

These results demonstrate that XA and dopamine are not co-released in the frontal area, although XA modulates dopamine release. XA is therefore released by nerve terminals which are probably specific and modulates dopamine release via receptors situated at dopaminergic synapses, either in the dopaminergic nuclei themselves (VTA and SNc), or in nerve terminals controlling glutamate and/or GABA release in the frontal cortex. Quantitative autoradiography revealed the existence of high-affinity XA binding sites in both the frontal cortex and in mesencephalic dopaminergic nuclei.

2) Modification of Frontal Extracellular Release of Glutamate (GLU) and GABA After Retrodialysis of 20 µM XA for 20 Minutes The aim here was to investigate whether XA can modify glutamate and/or GABA release. Such modifications would then affect dopamine release. According to this hypothesis, XA receptor sites would be found on glutamate and/or GABA neurons in the frontal cortex.

a) Measurement of Amino Acid Concentrations in the Dialysates

Amino acids contained in 15 µl of dialysate were separated according to their hydrophobicity by reverse phase high performance liquid chromatography (HPLC). The system comprised a degasser (Waters In-Line Degasser), a pump (Waters 626 Pump, Waters 600 S Controller), a refrigerated CMA/200 sampler-injector (Refrigerated Microsampler, CMA/microdialysis, Carnegie) fitted with a 51 µl loop, a Nucleosil C18 column (5 µm, 25×0.4 cm), an oven (Waters), and a fluorimeter (Waters 470 scanning fluorescence detector). The mobile phase was composed of a binary gradient between solution A: 0.05 M $NaH_2PO_4$ (Roth) 80% (pH 4.8 adjusted with 10 N NaOH), methanol 20% (Chromanorm, Prolabo); and solution B: 0.05 M $NaH_2PO_4$ 20% (pH 4.8 ajusted with 10 N NaOH), methanol 80% and THF 5%. Glutamate and GABA were measured by fluorimetric detection at an excitation wavelength of 345 nm and an emission wavelength of 455 nm after derivatization. Chromatogram acquisition and quantitative data analysis were done with Millenium software (Waters).

The samples were derivatized by mixing 15 µl of dialysate with 15 µl of the following derivatization solution: 7.5 mg o-phthaldialdehyde (Sigma) in 4.5 ml of 0.1 M sodium tetraborate pH 9.3, 500 µl of methanol and 10 µl of 3-mercapto-propionic acid (Sigma). The elution rate was 0.8 ml/min at 35° C. in a series of steps: 90% A and 10% B at 0 min; 40% A and 60% B to 15 min (linear gradient); 40% A and 60% B to 19 min (isocratic gradient); 0% A and 100% B to 19.1 min; 0% A and 100% B to 24 min (isocratic gradient); 90% A and 10% B to 24.1 min (isocratic gradient) and 90% A and 10% B to 30 min. The limit of detection for glutamate and GABA in the samples was 0.75 fmoles (0.05 µM). β-amino-isobutyric acid (Sigma) was used as internal standard.

Results:

Retrodialysis of 20 µM XA for 20 minutes in the frontal cortex led to an immediate 37%±1 decrease in GLU release during 90 minutes before gradually returning to baseline. The results shown in FIGS. 35 and 36 are expressed as %±SEM (n=2). The 100% value (1 nmole/20 µl) represents the mean of four consecutive samples before stimulation.

10. Consequences of Stress Induced by Intermittent Electric Shock on Norepinephreine (NE) and XA Release in the Median Prefrontal Cortex (PFC)

This study was based on the hypothesis that norepinephrine (NE) in the prefrontal cortex coming from the locus caeruleus (A6) plays an important role in the individual behavioral differences in reactivity to stress. As the A6 nucleus was labelled with tritiated XA in the autoradiography studies, the aim was to see whether frontal release of XA could be involved in the mechanisms of electric shock-induced stress in animals.

Since spontaneous locomotor activity in a new environment is a behavioral indicator of reactivity to a stressor, we selected "responder animals" exhibiting a more marked behavioral response in this test.

The main components of the stress response are extrahypothalamic release of CRH (corticotropin releasing hormone) leading to stimulation of tyrosine hydroxylase (TH) which results in increased norepinephrine in the locus caerulerus and consequently increased NE release at nerve terminals (prefrontal cortex, amygdala and dentate gyrus).

Protocol:

1) Selection of Animals in the Open Field Test:

Number of squares crossed in a 5 minute session: 55.08±22.6 (6.53)

Mean±SD (SEM) n=12 Wistar rats weighing 350 g.

2) Stress and Neurochemical Quantification:

Stress was induced by intermittent electric shocks to the paw at a rate of 1 shock of 0.3 mA per min for 20 minutes.

Norepinephrine release in the prefrontal cortex was measured using the intracerebral microdialysis method on conscious animals coupled to a high performance liquid chromatography system with electrochemical detection.

Results:

The results are given in FIG. 37.

During the duration of the stress induced by intermittent electric shocks of 300 µA for 1 sec per minute for 20 minutes, norepinephrine release in the prefrontal cortex increased by +151% relative to baseline release and XA release increased by +250%.

These findings indicate that norepinephrine and XA are released concomitantly in the frontal cortex of stressed animals. Release of XA might be a stress adaptation reaction and administration of XA receptor agonists in stress situations may represent a novel therapeutic solution, especially since dopamine release is very low and XA and XA receptor agonists increase this release.

11. Neuropharmacological characterizations of XA Receptor Antagonists: study of the antagonist NCS-486

1) Study of Dopaminergic Stereotypies Induced by Intracerebral Injection of XA and Reversal by the Antagonist NCS-486

"Stereotypies" are involuntary movements made by the animal after administration of direct (apomorphine) or indirect (amphetamine) dopaminergic agonists.

The following stereotypies are observed: licking, chewing, hyperactivity, exploring, standing, grooming, burrowing, stretching and sniffing.

Effects of Xanthurenic Acid:

Intracerebral injections of XA in the striatum, VTA, lateral ventricles or nucleus accumbens induced dose-dependent stereotypies (doses injected: 2, 10, 50, 100 and 150 µg/rat). These behaviors developed two minutes after the intracerebral injection and lasted for 30 to 40 minutes. One hour after such behaviors disappeared, they could be re-induced by another injection.

After neurotoxic lesion of the mesencephalic nuclei ($A_9$–$A_{10}$) induced by 6-OHDA, injection of XA 25 mg/kg i.p. did not modify the number of controlateral rotations induced by apomorphine 0.1 mg/kg s.c. Similarly, XA 25 mg/kg had no effect on the number of ipsilateral rotations induced by administration of amphetamine.

Effects of NCS-486 on stereotypies induced by XA, apomorphine or amphetamine:

NCS-486 at a dose of 2 µg/rat i.c.v. completely antagonized the stereotypies induced by XA 2 µg i.c.v., whereas injection of NCS-486 alone (2 µg i.c.v.) had no effect on the animals' behavior.

After i.p. or i.c.v. injection, NCS-486 did not antagonize stereotypies induced by apomorphine 0.5 mg/kg s.c. On the other hand, NCS-486, at a dose of 200 mg/kg i.p. injected 30 minutes before XA 2 µg i.c.v. suppressed or strongly reduced the stereotypies.

2) Study of NCS-486 on General Activity of the Animals Measured in the Open Field Test and Reversal of XA-Induced Sedation This study showed that NCS-486 100 mg/kg p.o produced hyperactivity in the animals 1 hour after administration. Furthermore, NCS-486 was able to antagonize the sedation induced by i.p. injection of XA 100 mg/kg.

The results are presented in the following table:

| Behavior | Controls | Treated with NCS-486 | Variations in % |
| --- | --- | --- | --- |
| Gromming | 1 ± 1 | 3 ± 1 | — |
| Jumping | 1 ± 2 | 2 ± 2 | — |
| Standing | 20 ± 14 | 32 ± 1 | — |
| Total squares | 55 ± 37 | 143 ± 2** | +260 |
| Outer squares | 51 ± 33 | 128 ± 21* | +251 |
| Inner squares | 4 ± 4 | 14 ± 1* | +350 |
| Defecations | 2 ± 1 | 0 | — |

The results are given as the mean ± SD (n = 4 rats/group)
Student's test:
**p < 0.05;
**p < 0.01

Study of reversal of sedation induced by XA 100 mg/kg i.p

The results are presented in the following table:

| Behavior | Controls | XA 100 mg/kg (i.p.) | XA 100 mg/kg (i.p.) + ND-7002 100 mg/kg (per os) |
| --- | --- | --- | --- |
| Grooming | 4 ± 1 | 4 ± 2 | 4 ± 1 |
| Standing | 66 ± 4 | 37 ± 14 | 51 ± 11 |
| Total squares | 193 ± 22 | 110 ± 25* | 182 ± 15 |
| Outer squares | 153 ± 18 | 91 ± 17* | 148 ± 15 |
| Inner squares | 39 ± 9 | 19 ± 6 | 34 ± 8 |

The results are given as the mean ± SEM (n = 4 rats/group)
Student's test:
*p < 0.05

12. Characterization of the Neuropharmacological Activity of Ligands Binding to the Allosteric Site for Kynurenic Acid, an Integral Part of the XA Receptor Site: Example of Compound ND-7000, Derivative of Xanthurenic Acid or Kynurenic Acid Effects of ND-7000 on stereotypies induced by XA.

ND-7000 administered by intracerebroventricular injection at a dose of 20 µg/rat did not induce any stereotypies in the animals. At a dose of 50 µg/rat, ND-7000 induced considerable sedation. In contrast, simultaneous injection of 10 µg of ND-7000 and 10 µg of XA led to the appearance of stereotypies. A dose of 25 µg ND-7000+25 µg XA led to a very marked potentiation of stereotypies (grooming) and decreased the latency time to onset of these involuntary movements (2 minutes instead of 5 minutes).

Study of ND-7000 on general activity of the animals in the open field test

The test was performed 30 minutes after injection of the product at a dose of 100 or 200 mg/kg per os. The observation period was 15 minutes.

At both doses tested, global activity of the animals decreased in proportion to the dose.

The results are presented in the following table:

| Behavior | Controls | 100 mg/kg (i.p.) | 200 mg/kg (i.p.) |
| --- | --- | --- | --- |
| Grooming | 5 ± 4 | 3 ± 2 | 4 ± 2 |
| Standing | 53 ± 12 | 30 ± 6 (−44%) | 20 ± 9 (−63%) |
| Total squares | 215 ± 24 | 146 ± 15 (−33%) | 106 ± 22 (−51%) |
| Outer squares | 188 ± 35 | 129 ± 11 (−32%) | 97 ± 23 (−49%) |
| Inner squares | 27 ± 13 | 17 ± 8 (−38%) | 9 ± 7 (−68%) |

The results are given as the mean ± SD (n = 5 rats/group)

When administered at a dose of 100 to 200 mg/kg per os, ND-7000 did not induce catalepsy and did not alter reflex activities measured in sensorimotor tests.

The actograph obtained after administration of ND-7000 100 mg/kg per os (p.o.) is shown in FIG. 38.

In conclusion, the effects of ND-7000 on cerebral dopaminergic activities induced by XA and on global reactivity as measured in the open field test, suggest that this product potentiates XA binding to its receptor. These results confirm the binding studies showing a marked increase in XA binding to its receptor site in the presence of ND-7000.

These experiments provide pharmacological data confirming the existence of another pathway by which to potentiate the effects of XA: synthetic ligands which bind to the allosteric site. Negative allosteric effectors, antagonist of the binding of ND-7000 and kynurenic acid derivatives, which would reduce XA activity by decreasing its binding to its receptor site, might also be envisioned. This represents a novel avenue of research for the synthesis of original ligands.

13. An Example of an XA Receptor Agonist Ligand, a Xanthurenic Acid Derivative Named ND-1301

ND-1301 was chosen to illustrate the series of XA receptor agonist ligands. This substance displaced radiolabelled XA from its binding site with good affinity and induced a strong electrophysiological response in patch-clamp tests in NCB-20 cells. Oral administration of ND-1301 to animals also modulated dopamine levels in brain tissue, as shown by the results hereinbelow.

FIG. 39 illustrates the dose-response effect observed after p.o. administration of ND-1301 on dopamine tissue levels in different brain regions.

The invention claimed is:

1. A method for selecting, identifying or characterizing compounds that inhibit the binding of xanthurenic acid (XA) to proteins that bind XA, comprising:
   contacting a test compound with brain cell membranes containing proteins which specifically bind XA, wherein said membranes are obtainable by the process comprising the following steps:
   (a) preparing synaptosomes by brain cells homogenisation to produce a homogenate, and
   (b) recovering said brain cell membranes from said homogenate; and
   measuring the inhibition of the binding of xanthurenic acid to said proteins by said test compound, said measuring comprising
   (1) determining the binding of XA to the brain cell membrane proteins by contacting a labeled XA with brain cell membrane containing said proteins,
   (2) determining the binding of labeled XA to brain cell membrane proteins in the presence of a test compound, and
   (3) comparing the binding in (1) with the binding in (2) as an indication of said inhibition.

2. A method according to claim 1, wherein
step (a) comprises the following steps:
   lysis of a brain sample to produce a lysate, and
   centrifugation of the lysate to produce a pellet comprising synaptosomes; and
step (b) comprises the following steps:
   disruption of the synaptosomes to produce brain cell membranes, and separation of the brain cell membranes.

3. The method of claim 1 wherein step (a) further comprises lysis of a brain sample and centrifugation of the obtained lysate to provide synaptosomes, and step (b) further comprises disruption of said synaptosomes to produce a brain cell membrane containing composition and recovering said brain cell membranes from said brain cell membrane containing composition.

4. A method according to claim 3, wherein
step (a) comprises the following steps:
   homogenizing said brain samples in a volume of a solution S equal to 10× the weight of said brain sample (S=0.32 M sucrose, 10 mM $KH_2PO_4$ pH 6.0, 1 mM EDTA) to produce a homogenate sample,
   centrifuging said homogenate sample at 915 g at 4° C. for 10 minutes to produce a first pellet and a first supernatant,
   separating the first supernatant from said first pellet to produce a separated first supernatant, and
   centrifuging said separated first supernatant at 18,200 g at 4° C. for 20 minutes to produce a second pellet and a second supernatant; and
step (b) comprises the following steps:
   separating the second supernatant and the second pellet to produce a separated second pellet, wherein said separated second pellet comprises synaptosomes,
   rupturing said synaptosomes in said separated second pellet by admixing a volume of distilled water at 0° C. equal to 70× the weight of said separated second pellet and homogenizing for 30 seconds, to produce disrupted synaptosomes in a homogenized composition,
   recovering said disrupted synaptosomes from said homogenized composition by centrifuging said homogenized composition at 51,000 g at 4° C. for 20 minutes and separating a pellet produced by said centrifuging, said pellet containing said disrupted synaptosomes,
   washing said pellet in 50 mM $KH_2PO_4$ buffer pH 6.0 at 0° C. to produce a washed pellet composition and centrifuging said washed pellet composition at 51,000 g at 4° C. for 20 minutes to produce a supernatant and said brain cell membrane containing composition in the form of a pellet, and
   recovering said brain cell membrane containing composition in the form of a pellet.

5. A method according to claim 1, wherein said brain cell membranes are synaptic membranes.

* * * * *